(12) United States Patent
Shaul et al.

(10) Patent No.: US 9,840,711 B2
(45) Date of Patent: *Dec. 12, 2017

(54) METHODS OF TREATING CANCER

(71) Applicant: Yeda Research and Development Co. Ltd., Rehovot (IL)

(72) Inventors: Yosef Shaul, Rehovot (IL); Peter Tsvetkov, Rehovot (IL); Julia Adler, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,784

(22) Filed: Feb. 27, 2017

(65) Prior Publication Data

US 2017/0175127 A1  Jun. 22, 2017

Related U.S. Application Data

(62) Division of application No. 14/866,957, filed on Sep. 27, 2015, now Pat. No. 9,579,339, which is a division of application No. 14/354,580, filed as application No. PCT/IL2012/050422 on Oct. 25, 2012, now Pat. No. 9,145,559.

(60) Provisional application No. 61/551,970, filed on Oct. 27, 2011.

(51) Int. Cl.
*A61K 48/00* (2006.01)
*C12N 15/113* (2010.01)

(52) U.S. Cl.
CPC ...... *C12N 15/1137* (2013.01); *C12N 2310/14* (2013.01)

(58) Field of Classification Search
None
See application file for complete search history.

(56) References Cited

U.S. PATENT DOCUMENTS

| 9,145,559 B2 | 9/2015 | Shaul et al. |
| 2014/0288157 A1 | 9/2014 | Shaul et al. |
| 2016/0008390 A1 | 1/2016 | Shaul et al. |

FOREIGN PATENT DOCUMENTS

| WO | WO 2005/028676 | 3/2005 |
| WO | WO 2005/103254 | 11/2005 |
| WO | WO 2008/039937 | 4/2008 |
| WO | WO 2009/099991 | 8/2009 |
| WO | WO 2009/117196 | 9/2009 |
| WO | WO 2013/061328 | 5/2013 |

OTHER PUBLICATIONS

Communication Pursuant to Article 94(3) EPC dated Aug. 25, 2016 From the European Patent Office Re. Application No. 12784743.2.
Communication Relating to the Results of the Partial International Search dated Feb. 7, 2013 From the International Searching Authority Re. Application No. PCT/IL2012/050422.
International Preliminary Report on Patentability dated May 8, 2014 From the International Bureau of WIPO Re. Application No. PCT/IL2012/050422.
International Search Report and the Written Opinion dated Apr. 22, 2013 From the International Searching Authority Re. Application No. PCT/IL2012/050422.
Office Action Dated Feb. 28, 2017 From the Israel Patent Office Re. Application No. 232266 and Its Translation Into English. (11 Pages).
Official Action dated Jun. 3, 2016 From the US Patent and Trademark Office Re. U.S. Appl. No. 14/866,957.
Official Action dated Jan. 23, 2015 From the US Patent and Trademark Office Re. U.S. Appl. No. 14/354,580.
Adams "Proteasome Inhibition: A Novel Approach to Cancer Therapy", Trends in Molecular Medicine, XP003004500, 8(4): S49-S54, Jan. 1, 2002.
Byrne et al. "Knockdown of Human Deubiquitinase PSMD14 Induces Cell Cycle Arrest and Senescence", Experimental Cell Research, XP055051181, 316(2): 258-271, Jan. 15, 2010.
Landis-Piwowar et al. "A Novel Prodrug of the Green Tea Polyphenol (−)-Epigallocatechin-3-Gallate as a Potential Anticancer Agent", Cancer Research, XP002664870, 67(9): 4303-4310, May 1, 2007.
Lin et al. "Curcumin Inhibits Tumor Growth and Angiogenesis in Ovarian Carcinoma by Targeting the Nuclear Factor-KB Pathway", Clinical Cancer Research, XP055296333, 13(11): 3423-3430, Jun. 1, 2007.
Matsuyama et al. "Proteasomal Non-Catalytic Subunit PSMD2 as a Potential Therapeutic Target in Association With Various Clinicopathologic Features in Lung Adenocarcinomas", Molecular in Carcinogenesis, XP055051487, 50(4): 301-309, Apr. 1, 2011.
Meng et al. "Gankyrin Promotes the Proliferation of Human Pancreatic Cancer", Cancer Letters, XP027254158, 297(1): 9-17, Nov. 1, 2010.
Yamada et al. "Inhibition of TRIP1/S8/hSug1, A Component of the Human 19S Proteasome, Enhances Mitotic Apoptosis Induced by Spindle Poisons", Molecular Cancer Therapeutics, XP055051183, 5(1): 29-38, Jan. 23, 2006.

*Primary Examiner* — Kimberly Chong

(57) ABSTRACT

A method of treating cancer is disclosed. The method comprises administering to the subject a therapeutically effective amount of a pharmaceutical composition comprising an agent which induces a dissociation of the 26S proteasomal complex into a 20S component and a 19S component to thereby inhibit 26S proteasomal activity, wherein the pharmaceutical agent is devoid of a chemotherapeutic agent.

4 Claims, 14 Drawing Sheets
(4 of 14 Drawing Sheet(s) Filed in Color)

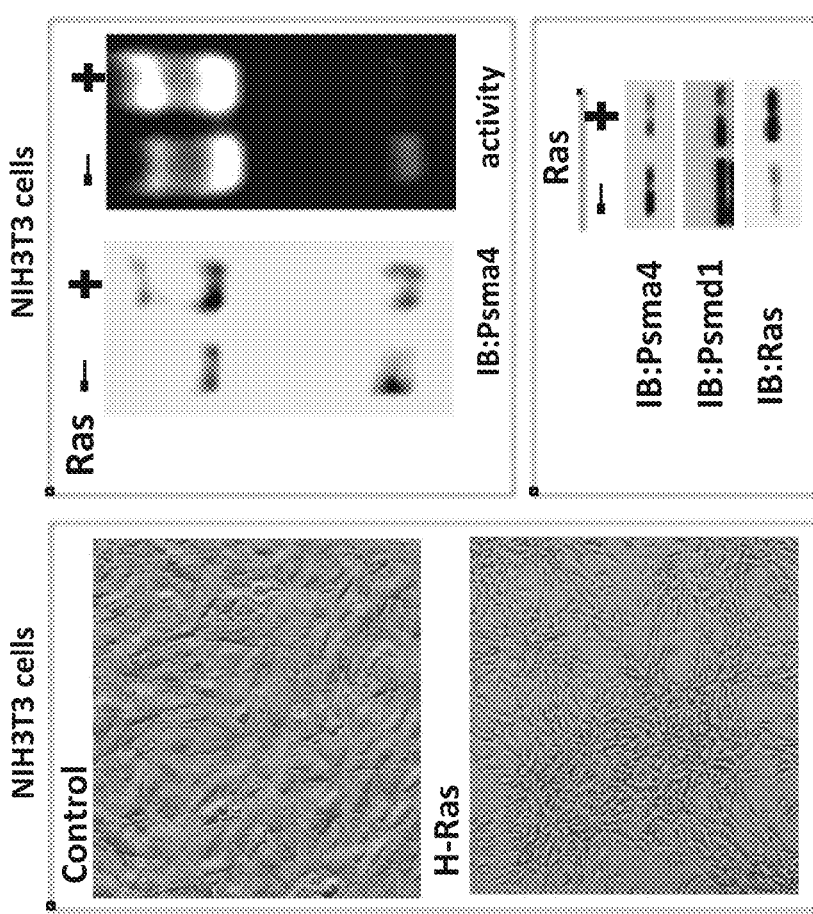

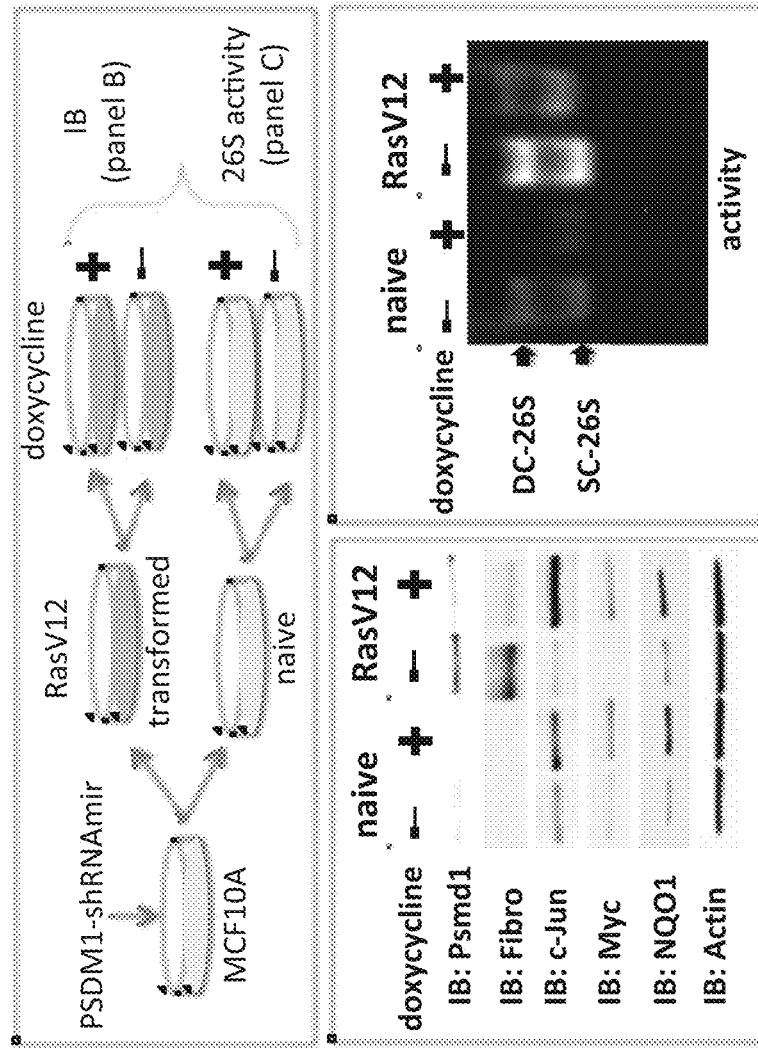

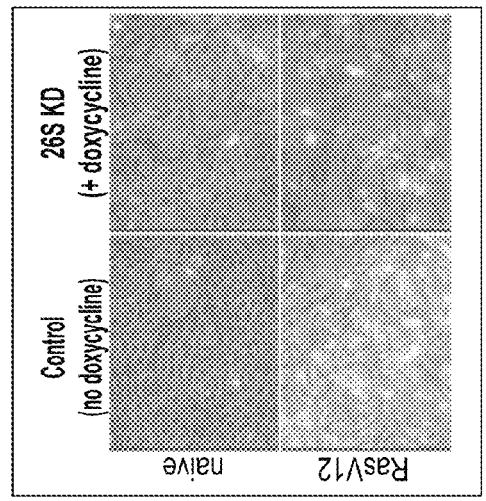
FIG. 4A
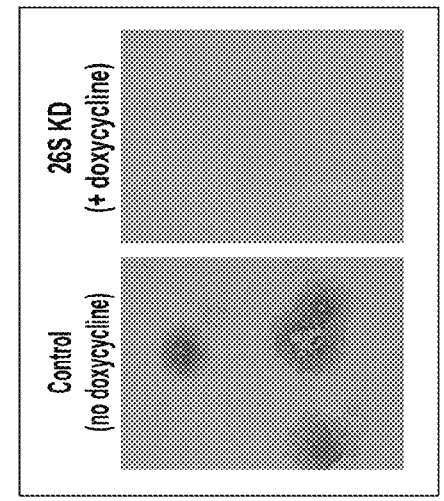
FIG. 4C
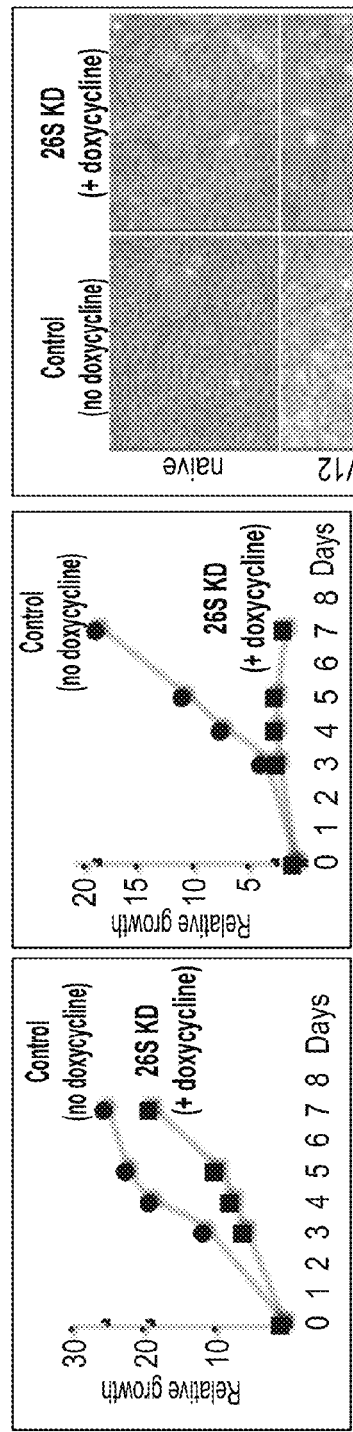
FIG. 4B
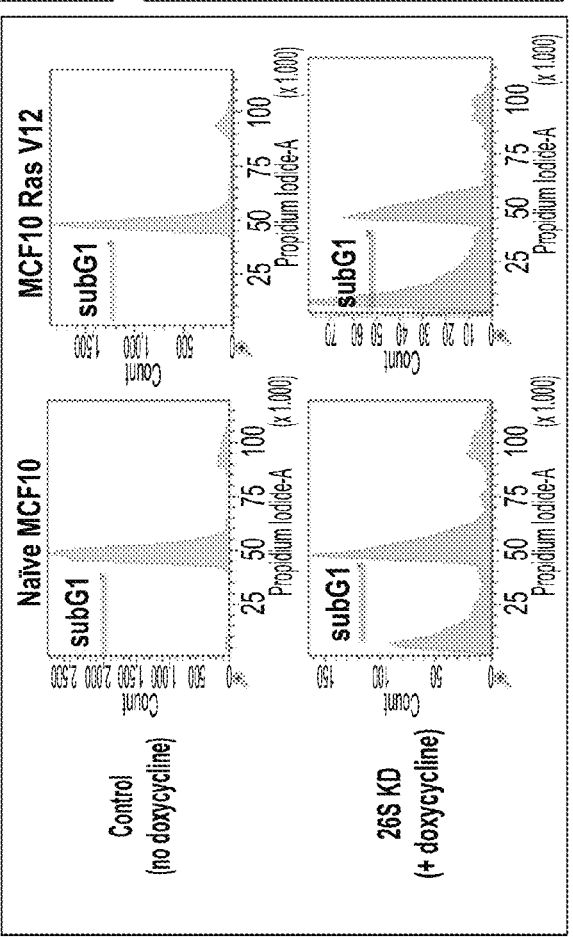
FIG. 4D
FIG. 4E

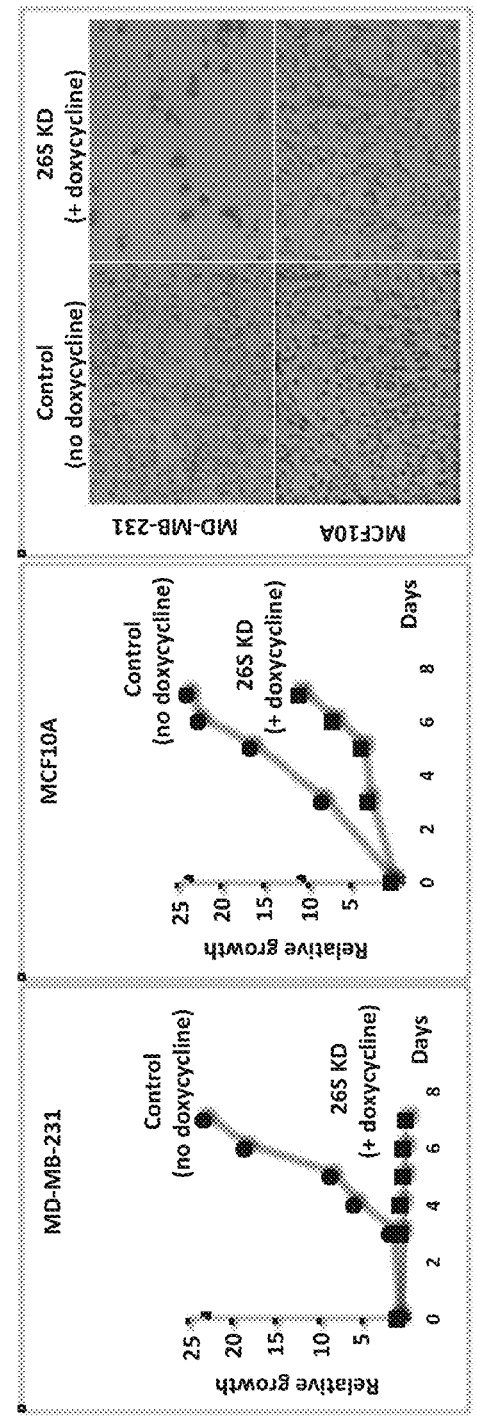
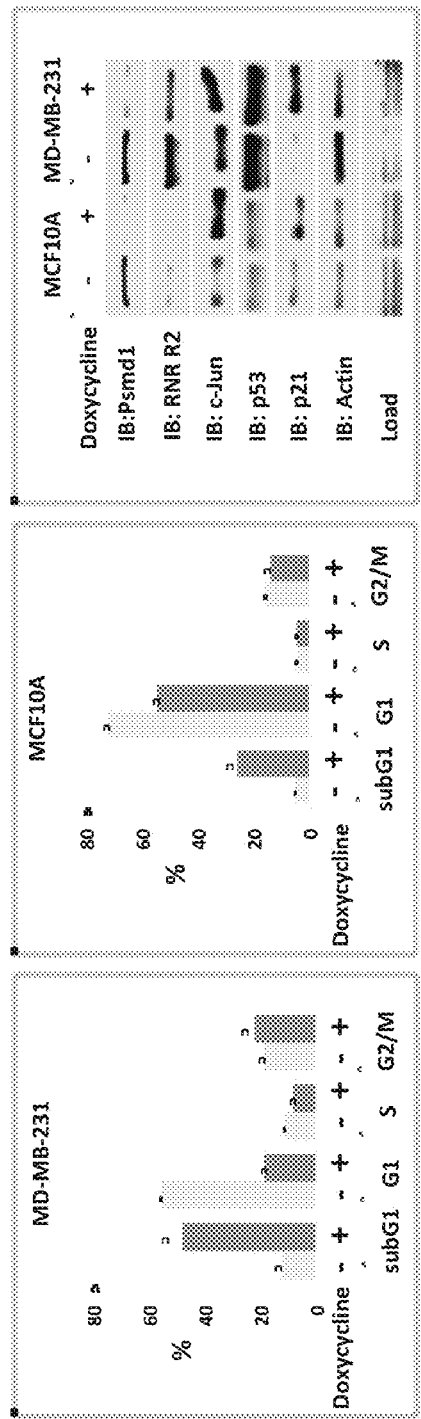
FIG. 5A  FIG. 5B  FIG. 5C
FIG. 5D  FIG. 5E  FIG. 5F

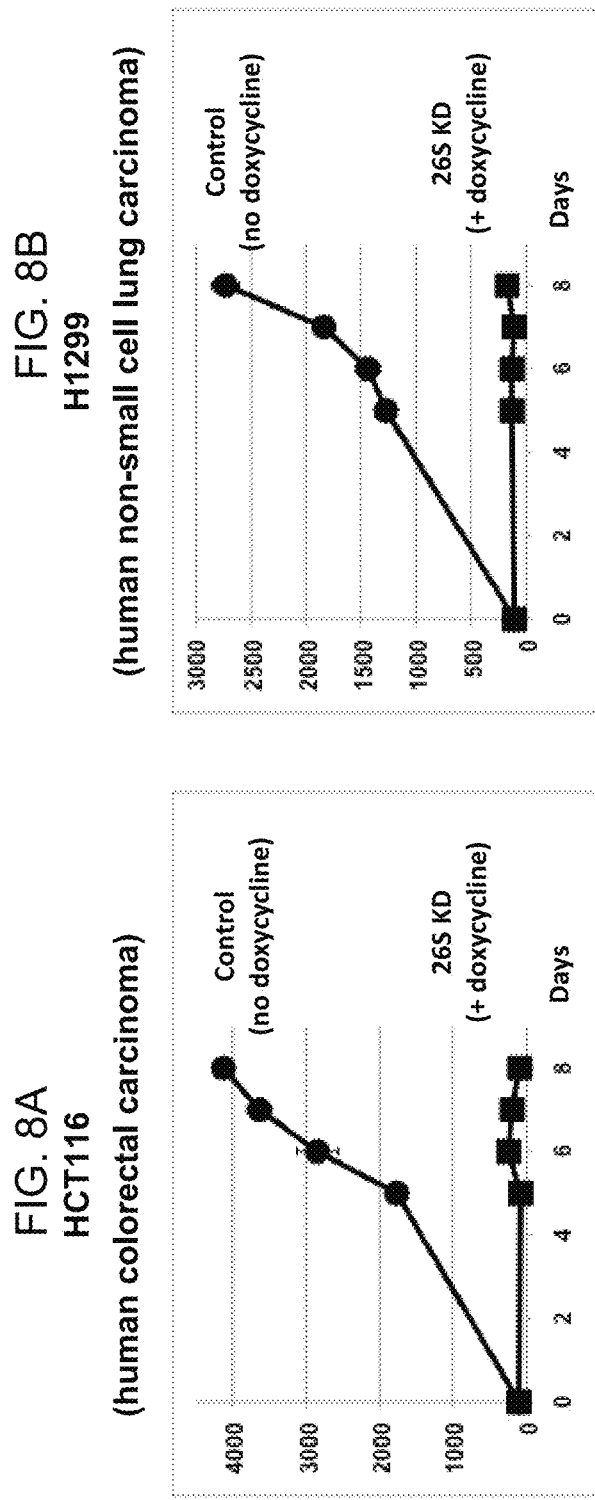
FIG. 8A HCT116 (human colorectal carcinoma)
FIG. 8B H1299 (human non-small cell lung carcinoma)

US 9,840,711 B2

METHODS OF TREATING CANCER

RELATED APPLICATIONS

This application is a Division of U.S. patent application Ser. No. 14/866,957 filed on Sep. 27, 2015, which is a Division of U.S. patent application Ser. No. 14/354,580, filed on Apr. 27, 2014, now U.S. Pat. No. 9,145,559, which is a National Phase of PCT Patent Application No. PCT/IL2012/050422 having International Filing Date of Oct. 25, 2012, which claims the benefit of priority under 35 USC §119(e) of U.S. Provisional Patent Application No. 61/551,970 filed on Oct. 27, 2011. The contents of the above applications are all incorporated by reference as if fully set forth herein in their entirety.

SEQUENCE LISTING STATEMENT

The ASCII file, entitled 69332SequenceListing.txt, created on Feb. 26, 2017 comprising 34,164 bytes, submitted concurrently with the filing of this application is incorporated herein by reference.

FIELD AND BACKGROUND OF THE INVENTION

The present invention, in some embodiments thereof, relates to a method of treating diseases for which inhibiting a proteasome is advantageous by using agents, which specifically target the 19S proteasomal complex. Proteasomal protein degradation is crucial in maintaining cellular integrity and in regulating key cellular processes including cell cycle, proliferation and cell death. Proteasomal degradation is mediated mainly by two proteasomal complexes; the 26S proteasome, that consists of the 20S catalytic domain and two 19S regulatory particles (RP) and the 20S proteasome in isolation (1, 2). In the well-characterized ubiquitin-proteasome system (UPS) a protein is targeted for degradation by specific modification by a set of enzymes that conjugates a poly-ubiquitin chain to the protein. The poly-ubiquitinated substrate is then recognized by specific subunits of the 19S RP of the 26S proteasome where it is de-ubiquitinated, unfolded by the ATPases and translocated into the 20S catalytic chamber for degradation. Recently a ubiquitin-independent proteasomal degradation pathway has been described whereby intrinsically disordered proteins (IDPs) such as p53, c-FOS, BimEL (8-10) and others can be degraded by the 20S proteasome in a process that does not involve active ubiquitin tagging. The 20S proteasome has been also shown to be activated by the REG (11S) family members inducing the degradation of SRC-3, p21 and other proteins. Thus, there are at least two distinct proteasomal protein degradation pathways each regulated by the distinct 26S and 20S proteasomal complexes.

The UPS as a regulator of cell death has been a tempting target for drug development for many pathologies specifically cancer (14-16). Various tumors have been shown to express high levels of proteasomal subunits and higher proteasomal activity (17-19). A number of studies suggests that cancer cells exhibit high sensitivity to proteasomal inhibition (20). Sensitivity to proteasomal inhibition was specifically shown efficient in lymphoid malignancies, particularly multiple myeloma where the proteasomal inhibitor Brotezamide (VELCADE, PS-341) was approved for therapy (21-23). Proteasome inhibitors were also shown efficient in various screens of solid and hematologic tumors (24, 25) and currently there is an increasing number of cancers that are in the process of clinical trials with different proteasomal inhibitors (26). Proteasomal inhibitors such as Brotezamide, MG132, and β-lapachone inhibit the 20S proteasome (27) therefore these drugs inhibit the entire proteasomal activity including the 26S (that is comprised of the 20S and 19S) and the 20S proteasomal complexes.

Hiroshi Y et al [Mol Cancer Ther 2006; 5(1):29-38] teaches that targeting the ATPase subunits of the 19S regulatory complex in the proteasome enhances spindle poison—mediated cell killing in cancer cells.

Other background art includes Byrne A. et al. ECR 2010; 316:258-271 and International Patent Application WO2009117196.

SUMMARY OF THE INVENTION

According to an aspect of some embodiments of the present invention there is provided a method of treating a disease for which inhibiting a proteasome is advantageous, the method comprising administering to the subject a therapeutically effective amount of an agent which down-regulates an expression and/or activity of proteasome 26S subunit, non-ATPase selected from the group consisting of PSMD1, PSMD6 and PSMD11, thereby treating the disease.

According to an aspect of some embodiments of the present invention there is provided a method of treating ovarian or breast cancer, the method comprising administering to the subject a therapeutically effective amount of an agent which down-regulates an expression and/or activity of proteasome 26S subunit, non-ATPase, ATPase selected from the group consisting of PSMD1, PSMD6 and PSMD11, thereby treating the disease.

According to an aspect of some embodiments of the present invention there is provided a method of treating cancer, the method comprising administering to the subject a therapeutically effective amount of a pharmaceutical composition comprising an agent which induces a dissociation of the 26S proteasomal complex into a 20S component and a 19S component to thereby inhibit 26S proteasomal activity, wherein the pharmaceutical composition is devoid of a chemotherapeutic agent, thereby treating the cancer.

According to an aspect of some embodiments of the present invention there is provided a method of treating a disease for which inhibiting a proteasome is advantageous, the method comprising administering to the subject a therapeutically effective amount of a polynucleotide agent comprising a nucleic acid sequence selected from the group consisting of SEQ ID NO:2, SEQ ID NO: 14, SEQ ID NO: 15, SEQ ID NO: 16 and SEQ ID NO: 17.

According to an aspect of some embodiments of the present invention there is provided a pharmaceutical agent comprising an agent which down-regulates an amount or activity of proteasome 26S subunit, non-ATPase selected from the group consisting of PSMD1, PSMD6 and PSMD11 and a pharmaceutically acceptable carrier.

According to an aspect of some embodiments of the present invention there is provided a method of selecting an agent useful for treating a disease for which inhibiting a proteasome is advantageous, the method comprising:

(a) contacting the agent with a 26S proteasomal complex of a cell;

(b) analyzing an amount of dissociation of the 26S proteasomal complex into a 19S regulatory particle (RP) and a 20S subunit, wherein an upregulation of the dissociation compared to an amount of dissociation of the 26S proteasomal complex in an absence of the agent, is indicative of an agent useful for treating a disease for which inhibiting a proteasome is advantageous.

According to some embodiments of the invention, the agent comprises a polynucleotide agent directed against a 19S component of the 26S proteasomal complex.

According to some embodiments of the invention, the disease is cancer.

According to some embodiments of the invention, the disease is an inflammatory disease.

According to some embodiments of the invention, the disease is a neurodegenerative disease.

According to some embodiments of the invention, the cancer comprises breast cancer or ovarian cancer.

According to some embodiments of the invention, the agent comprises a polynucleotide agent directed against a polynucleotide encoding the PSMD.

According to some embodiments of the invention, the agent comprises a small molecule agent.

According to some embodiments of the invention, the polynucleotide agent comprises an siRNA.

According to some embodiments of the invention, the siRNA comprises a nucleic acid sequence selected from the group consisting of SEQ ID NO: 2, SEQ ID NO: 14, SEQ ID NO: 15, SEQ ID NO: 16 and SEQ ID NO: 17.

According to some embodiments of the invention, the polynucleotide agent comprises a nucleic acid sequence as set forth in SEQ ID NO: 3.

According to some embodiments of the invention, the pharmaceutical agent is devoid of a chemotherapeutic agent.

According to some embodiments of the invention, the agent comprises a polynucleotide agent directed against a polynucleotide encoding the PSMD.

According to some embodiments of the invention, the polynucleotide agent comprises an siRNA. According to some embodiments of the invention, the siRNA comprises a nucleic acid sequence selected from the group consisting of SEQ ID NO: 2, SEQ ID NO: 14, SEQ ID NO: 15, SEQ ID NO: 16 and SEQ ID NO: 17.

According to some embodiments of the invention, the analyzing is effected on the protein level.

According to some embodiments of the invention, the analyzing is effected on the polynucleotide level.

According to some embodiments of the invention, the disease is cancer.

According to some embodiments of the invention, the disease is an inflammatory disease.

According to some embodiments of the invention, the disease is a neurodegenerative disease.

According to some embodiments of the invention, the cancer comprises breast cancer or ovarian cancer.

According to an aspect of some embodiments of the present invention there is provided an agent which down-regulates an expression and/or activity of a proteasome 26S subunit, non-ATPase selected from the group consisting of PSMD1, PSMD6 and PSMD11 for use in treating a disease for which inhibiting a proteasome is advantageous.

According to an aspect of some embodiments of the present invention there is provided an agent which down-regulates an expression and/or activity of a proteasome 26S subunit, non-ATPase, selected from the group consisting of PSMD1, PSMD6 and PSMD11 for treating ovarian or breast cancer.

According to an aspect of some embodiments of the present invention there is provided a pharmaceutical composition comprising an agent which induces a dissociation of the 26S proteasomal complex into a 20S component and a 19S component to thereby inhibit 26S proteasomal activity, wherein the pharmaceutical composition is devoid of a chemotherapeutic agent for treating cancer.

According to an aspect of some embodiments of the present invention there is provided a polynucleotide agent comprising a nucleic acid sequence selected from the group consisting of SEQ ID NO:2, SEQ ID NO: 14, SEQ ID NO: 15, SEQ ID NO: 16 and SEQ ID NO: 17 for treating a disease for which inhibiting a proteasome is advantageous.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee. Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1C illustrate that the H-RAS V12 transformed NIH3T3 cells contain high level of 26S proteasome. A, NIH3T3 cells were transformed with retroviruses containing pBabe H-Ras V12 vectors, and visualized by microscopy. The cells displayed transformed phenotype with spindle-shaped and highly refractile morphology B, 26S and 20S proteasomal complex activity and level were analyzed by native gel electrophoresis in both naïve NIH3T3 and Ras transformed cells. To analyze the proteasome level we used the Psma4 antibody. Psma4 is a component of the 20S proteasome. C, expression of the proteasomal subunits PSMA4, a 20S component, and PSMD1, a 19S component, was quantified by immunoblot (IB). The level of the examined proteins did not alter significantly in the H-Ras V12 transformation process, whereas as expected higher level of Ras was detected in the Ras transformed cells.

FIGS. 3A-3C illustrate that Psmd1 knockdown decreased the 26S proteasome level in the Ras transformed cells. A. Schematic description of the experimental strategy. MCF10A stably expressing the doxycycline-induced knockdown of Psmd1shRNA was further subjected to transformation with H-Ras V12. Psmd1 KD was induced by the addition of 1 µg/ml doxy for 72 hours and the activity of the proteasomal complex was analyzed. B. Equal amount of protein were loaded on SDS-PAGE and analyzed for protein content in the MCF10A naive and H-Ras V12 transformed cells in the presence or absence of induction of Psmd1 KD for 72 hours. C. The level of the 26S proteasome activity was determined as described in FIG. 2C.

FIGS. 4A-4E illustrate that the Ras transformed MCF10A cells markedly undergo apoptosis by Psmd1 KD. A. Cell proliferation rate was analyzed using the XTT assay and confirmed by direct cell counting. Naïve MCF10A cells infected with a lentivector based Psmd1 knockdown were either doxycycline treated to induce Psmd1 shRNA expression or left untreated and cell proliferation was daily followed. B. Similar to A but this time the Ras transformed cells were analyzed. C. Cells were visualized 72 hours following induction of Psmd1 KD and representative pictures are shown. D. Cells were analyzed by FACS to evaluate cell death level by quantifying the subG1 fraction. E. Soft agar colony formation assay was performed and the data obtained 2 weeks after culturing of the H-Ras V12 MCF10A transformed cells in the presence or absence of induction of Psmd1 KD (addition of 1 µg/ml doxy), are shown. No colonies were obtained under Psmd1 KD.

FIGS. 5A-5F illustrate that MDA-MB-231 breast cancer cells are highly sensitive to Psmd1 KD. A. The drug resistant MDA-MB-231 breast cancer cells were infected with the lentivector expressing Psmd1 shRNA under doxycycline induction. Cell proliferation was quantified as described in FIG. 4A. B. MCF10A cells were used as a control. C. Cells were visualized in response to Psmd1 knockdown. D. Cell cycle distribution of MDA-MB-231 cells was quantified by FACS analysis in the presence or absence of doxycycline treatment to induce Psmd1 shRNA expression. E. As in panel D but naïve MCF10A cells were analyzed. F. Cells under different treatments were extracted and the level of proteins of interested was examined by immunoblotting.

FIGS. 8A-8B illustrate the sensitivity of human colorectal cancer cells (HCT116) or human non small cell lung carcinoma (H1299) cells to Psmd1 knockdown.

DESCRIPTION OF SPECIFIC EMBODIMENTS OF THE INVENTION

The present invention, in some embodiments thereof, relates to a method of treating diseases for which the specific downregulation of the 26S proteasomal complex is advantageous by using agents that can target the subunits of the 19S proteasomal particle which are involved in 26S proteasome assembly, ultimately resulting in the downregulation of the 26S proteasome.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Proteasomes are very large intracellular complexes active in the degradation of proteins. The major complex is the 26S particle that is formed by association of the 20S catalytic particle with one or two 19S regulatory particles (RP), although it is known that the 20S particle may also work independently of the 19S RP. The 26S proteasome degrades polyubiquinated substrates that are mostly components of the cycling cells, thus selective downregulation of the 26S proteasome formation without the disruption of the activity of the 20S could be beneficial in the induction of cancer cell death but not non-cancer cells.

Figures 2A, 2B, 2C:
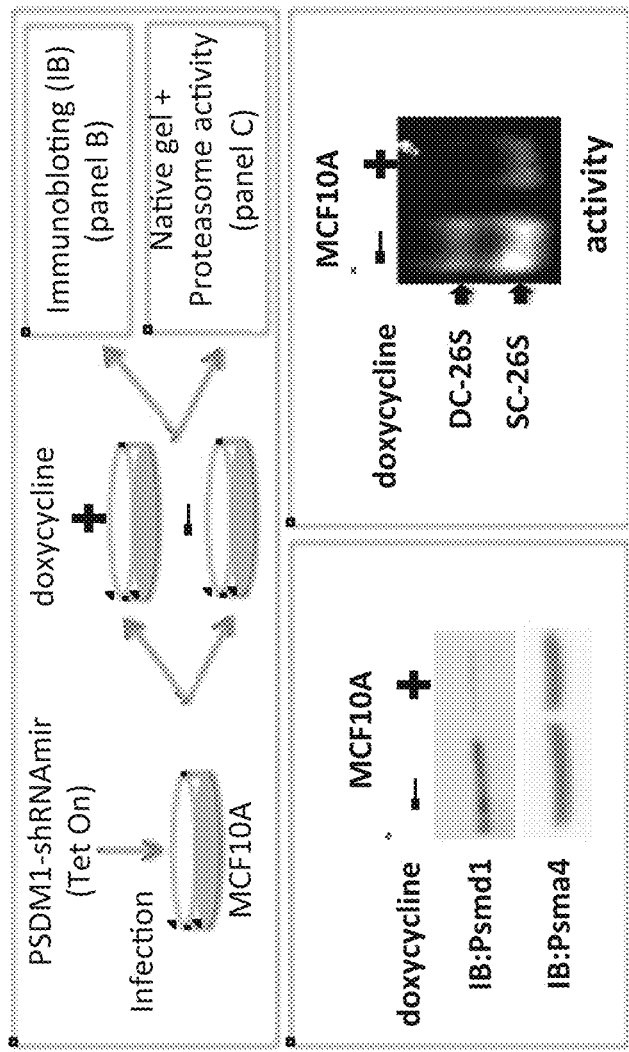
FIGS. 2A-2C illustrate that Psmd1 knockdown gives rise to low 26S proteasome level. A. Schematic description of the experimental strategy. Psmd1 KD was induced by the addition of 1 μg/ml doxycycline to MCF10A stably expressing the doxycycline-induced knockdown of Psmd1 shRNA, B. the levels of Psmd1 protein under these conditions were determined to validate efficacy of the knockdown process. C. The level of the 26S proteasome was determined by native gel analysis and in gel proteasome activity protocol 72 hours following the induction of the Psmd1 knockdown. The 26S complex is either double capped, namely each of the both ends of the 20S proteasome is occupied by a 19S complex (DC-26S) or single capped (SC-26S).

To this aim a component of the 19S RP necessary for its assembly with the 20S was targeted and its expression reduced. The present inventors found that knock-down of a particular gene (Psmd1) in the 19S regulatory complex leads to the downregulation of both the amount and the activity of the 26S particle, as illustrated in FIG. 2C. Remarkably, they found that this approach allowed for selective and highly effective killing of tumor cells compared with non-transformed cells (FIGS. 4A-4E).

Whilst reducing the present invention to practice, the present inventors showed that down-regulation of the 19S subunit of the proteasome selectively reduced 26S proteasomal activity, and was effective at killing MBA-MD-231 breast cancer cells (FIGS. 5A-5F) and OVCAR-3 ovarian cancer cells (FIGS. 7A-7C), both of which serve as good in vitro models for aggressive tumors that are resistant to most currently available cancer drugs.

Accordingly, the present inventors propose to use this strategy in cancer therapy of patients, including those that carry tumors that are refractory to presently available drugs.

Thus, according to one aspect of the present invention there is provided a method of treating a disease for which inhibiting a proteasome is advantageous. The method comprises administering to the subject a therapeutically effective amount of an agent which downregulates the amount or activity of the 26S proteasomal complex without disrupting the 20S catalytic domain.

According to one embodiment, the agent disrupts the 26S proteasomal complex by either inhibiting 26S assembly or inducing 26S dissociation into its components—the 20S and the 19S.

The disassembly and/or dissociation can be achieved by targeting subunits of the 19S regulatory particle (e.g. Psmd1, Psmd2 (Ref Seq No: $NM_{13}$ 002808—SEQ ID NO: 4; NP_002799), Psmd3 (Ref Seq No: NM_002809—SEQ ID NO: 5; NP_002800), Psmd4 (Ref Seq No: NM_002810—SEQ ID NO: 6; NP_002801), Psmd6 (Ref Seq No: NM_014814—SEQ ID NO: 7; NP_055629), Psmd7 (Ref Seq No: NM_002811—SEQ ID NO: 8; NP_002802), Psmd8 (Ref Seq No: NM_002812—SEQ ID NO: 9; NP_002803), Psmd11 (Ref Seq No: NM_002815—SEQ ID NO: 13; NP_002806) or Psmd12 (Ref Seq No: NM_002816.3—SEQ ID NO: 10; NP_002807.1).

According to one embodiment, the 19S subunit is not Psmd13.

Preferably the agents have at least a 5 fold higher binding affinity for a subunit of the 19S regulatory particle than a subunit of the 20S catalytic domain.

Preferably the agents have at least a 5 fold higher inhibitory activity for a subunit of the 19S regulatory particle than for a subunit of the 20S catalytic domain.

According to a particular embodiment, the agent is one which down-regulates an amount or activity of proteasome 26S subunit, non-ATPase, 1 (Psmd1).

According to a particular embodiment, the agent is one which down-regulates an amount or activity of Psmd6.

According to a particular embodiment, the agent is one which down-regulates an amount or activity of PSmd11.

According to this embodiment, the agent has at least a 5 fold higher binding affinity for Psmd1 than another subunit of the 19S regulatory particle.

As used herein the term "proteasome 26S subunit, non-ATPase, 1 (Psmd1)" refers to the protein present in the 19S regulatory unit of the 26S proteasome. In humans, it is encoded by the gene at chromosome location chr2:231,921,578-232,037,541, Ensembl gene No. ENSG00000173692, the mRNA transcript being as disclosed in Ref Seq Nos. NM_001191037.1—SEQ ID NO: 11 and NM_002807.3—SEQ ID NO: 12. There are two splice variants of this gene—resulting in two proteins provided by Swiss Prot. No. Q99460-1 and Q99460-2.

Downregulation of PSMD1 (or any one of the targets listed above) can be effected on the genomic and/or the transcript level using a variety of molecules which interfere with transcription and/or translation [e.g., RNA silencing agents (e.g., antisense, siRNA, shRNA), Ribozyme and DNAzyme], or on the protein level using e.g., antagonists, enzymes that cleave the polypeptide and the like.

Following is a list of agents capable of downregulating expression level and/or activity of Psmd1.

One example, of an agent capable of downregulating Psmd1 is an antibody or antibody fragment which specifically binding Psmd1 protein. Preferably, the antibody specifically binds at least one epitope of Psmd1. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that since the PSMD1 protein is an intracellular protein the antibody may be modified such that it is capable of working within the cell. The antibody may be a single-chain antibody (scFv), comprise a modification of immunoglobulin VL domains for hyperstability may be selected such that it is resistant to the more reducing intracellular environment, may be expressed as a fusion protein with maltose binding protein or other stable intracellular proteins.

In order to allow the antibody to work intracellularly, the antibody may be expressed in the cells of interest (i.e. using an expression construct, as further described herein below).

As mentioned, downregulation of PSMD1 may also be effected on the genomic and/or transcript level. Typically, these methods rely on the use of polynucleotides which are capable of hybridizing to the DNA or mRNA encoding PSMD1 under physiological conditions.

The term "polynucleotide" refers to a single-stranded or double-stranded oligomer or polymer of ribonucleic acid (RNA), deoxyribonucleic acid (DNA) or mimetics thereof. This term includes polynucleotides and/or oligonucleotides derived from naturally occurring nucleic acids molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to respective naturally occurring portions.

The length of the polynucleotide of the present invention is optionally of 100 nucleotides or less, optionally of 90 nucleotides or less, optionally 80 nucleotides or less, optionally 70 nucleotides or less, optionally 60 nucleotides or less, optionally 50 nucleotides or less, optionally 40 nucleotides or less, optionally 30 nucleotides or less, e.g., 29 nucleotides, 28 nucleotides, 27 nucleotides, 26 nucleotides, 25 nucleotides, 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, optionally between 12 and 24 nucleotides, optionally between 5-15, optionally, between 5-25, most preferably, about 20-25 nucleotides.

The polynucleotides (including oligonucleotides) designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

It will be appreciated that a polynucleotide comprising an RNA molecule can be also generated using an expression vector as is further described hereinbelow.

Preferably, the polynucleotide of the present invention is a modified polynucleotide. Polynucleotides can be modified using various methods known in the art.

For example, the oligonucleotides or polynucleotides of the present invention may comprise heterocyclic nucleosides consisting of purines and the pyrimidines bases, bonded in a 3'-to-5' phosphodiester linkage.

Preferably used oligonucleotides or polynucleotides are those modified either in backbone, internucleoside linkages, or bases, as is broadly described hereinunder.

Specific examples of preferred oligonucleotides or polynucleotides useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216, 141; 5,235,033; 5,264,562; 5,264,564; 5,405,938; 5,434, 257; 5,466,677; 5,470,967; 5,489,677; 5,541,307; 5,561, 225; 5,596,086; 5,602,240; 5,610,289; 5,602,240; 5,608, 046; 5,610,289; 5,618,704; 5,623,070; 5,663,312; 5,633, 360; 5,677,437; and 5,677,439.

Other oligonucleotides or polynucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Additionally, or alternatively the oligonucleotides/polynucleotide agents f the present invention may be phosphorothioated, 2-o-methyl protected and/or LNA modified.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990),"The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

The modified polynucleotide of the present invention may also be partially 2'-oxymethylated, or more preferably, is fully 2'-oxymethylated.

According to one embodiment, downregulation of PSMD1 is achieved by RNA silencing.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Exemplary antisense oligonucleotides generated from shRNAs include:

TAAGCATTCCCAATATGAG (SEQ ID NO: 2) for targeting to Psmd1;
AATAAACCTGGACAGTTCCTG (SEQ ID NO: 14) for targeting to Psmd6;
AATGACCTATATGATTCCAGC (SEQ ID NO: 15) for targeting to Psmd6;
ATAATACCCGACTGCATGTCC (SEQ ID NO: 16) for targeting to Psmd11;
ATAATTTCCTTTCCACGTCGG (SEQ ID NO: 17) for targeting to Psmd11.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with some embodiments of the invention can be effected as follows. First, the Psmd1 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level.

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable Psmd1 siRNA can be the siRNA Sense: CTCATATTGGGAATGCTTA (SEQ ID NO: 1); anti Sense: TAAGCATTCCCAATATGAG (SEQ ID NO: 2).

As mentioned, the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

Administration of dsRNA may be effected by administering the ds molecule itself or via an expression construct which encodes a single hairpin mRNA. This molecule is eventually processed in the cell to form a dsRNA product. Use of expression constructs is further described herein below.

Another agent capable of downregulating PSMD1 is a DNAzyme molecule capable of specifically cleaving an mRNA transcript or DNA sequence of the PSMD1. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www(dot)asgt(dot)org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of PSMD1 can also be effected by using an antisense polynucleotide capable of specifically hybridizing with an mRNA transcript encoding the PSMD1 protein.

Design of antisense molecules which can be used to efficiently downregulate a PSMD1 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating PSMD1 is a ribozyme molecule capable of specifically cleaving an mRNA transcript encoding a PSMD1. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation.

An additional method of regulating the expression of the PSMD1 gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
|---|---|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the psmd-1 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence—and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

As mentioned, the downregulating agents described hereinabove may be administered to the subject per se or may be expressed in the cells of the subject using gene therapy (i.e. with expression constructs).

DNA sequences are typically inserted into expression vectors to enable expression of the recombinant polypeptide or mRNA. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Recombinant viral vectors may also be used to synthesize the polynucleotides of the present invention. Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Bone marrow cells can be targeted using the human T cell leukemia virus type I (HTLV-I).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. According to a particular embodiment, the virus is a lentivirus. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Other agents which down-regulate the activity of PSMD1 are also contemplated by the present invention including small molecules.

"Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

The agents described herein down-regulate expression and/or activity of PSMD1 and lead to inhibition of the 26S proteasome.

Because unregulated, proteasome-mediated degradation of vital cell cycle regulatory proteins is an essential component of tumor development, a possible way of arresting or limiting tumor development is by inhibition of the proteasome. Proteasome inhibition leads to the stabilization of these substrates, and, as a result, cell-cycle arrest occurs and the cells ultimately undergo apoptosis. Transformed cells seem to be particularly sensitive to any disturbances of the cell cycle and/or the coordinated production and degradation of all proteins involved in this process, including proteasome inhibitor-induced growth retardation. Consequently, proteasome inhibitors are being actively explored for the treatment of a variety of hematologic malignant neoplasms and solid tumors.

Thus, according to one embodiment, the disease in which inhibiting a proteasome is advantageous is cancer.

Examples of cancers that may be treated using the 19S-specific proteasome inhibitors of this aspect of the present invention include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a specific embodiment, the cancer is breast cancer or ovarian cancer.

The formation of new blood vessels, angiogenesis, is critical for the progression of many diseases, including cancer metastases, diabetic retinopathy, and rheumatoid arthritis. Many factors associated with angiogenesis, eg, cell adhesion molecules, cytokines, and growth factors, are regulated through the proteasome, and, hence, alteration of its activity will affect the degree of vessel formation. Oikawa et al [Biochem Biophys Res Commun. 1998; 246:243-248] demonstrated that a particular proteasome inhibitor, lactacystin significantly reduced angiogenesis, suggesting that it, or related compounds, could be beneficial in disease states that rely on the formation of new blood vessels.

Thus, according to another embodiment, the disease in which inhibiting a proteasome is advantageous is an angiogenesis associated disease.

The proteasome is intimately linked to the production of the majority of the class I antigens. It is therefore conceivable that excessive inhibition of the proteasome might also increase the chance of viral infections such as HIV.

Through its regulation of NF-kappa B, the proteasome is central to the processing of many pro-inflammatory signals. Once released from its inhibitory complex through proteasome degradation of I kappa B, NF-kappa B induces the activation of numerous cytokines and cell adhesion molecules that orchestrate the inflammatory response. Thus, the present invention contemplates use of the proteasome inhibitors of the present invention for the treatment of inflammatory diseases including but not limited to asthma, ischemia and reperfusion injury, multiple sclerosis, rheumatoid arthritis, psoriasis, autoimmune thyroid disease, cachexia, Crohn disease, hepatitis B, inflammatory bowel disease, sepsis, systemic lupus erythematosus, transplantation rejection and related immunology and autoimmune encephalomyelitis.

In addition, it has been shown that blocking proteasome activity reduces neuron and astrocyte degeneration and neutrophil infiltration and therefore can be potential therapy for stroke and neurodegenerative diseases including Parkinson's disease, Alzheimer disease, and amyotrophic lateral sclerosis (ALS).

The 19S-specific proteasome inhibitors of this aspect of the present invention may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the proteasome inhibitors accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions that can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (proteasome inhibitor) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer, as further detailed below. Such information can be used to more accurately determine useful doses in humans.

Toxicity and therapeutic efficacy of the active ingredients described herein can be determined by standard pharmaceutical procedures in vitro, in cell cultures or experimental animals, as further detailed below. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure blood or tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned, various animal models may be used to test the efficacy of the agent of the present invention. A transgenic mouse model for cancer (e.g., breast cancer) such as the erb model (Shah N., et al., 1999, Cancer Lett. 146: 15-2; Weistein E J., et al., 2000, Mol. Med. 6: 4-16) or MTV/myc model (Stewart T A et al., 1984, Cell, 38: 627-637), the c-myc model (Leder A., et al., 1986, Cell, 45:485-495), v-Ha-ras or c-neu model (Elson A and Leder P, 1995, J. Biol. Chem. 270: 26116-22) can be used to test the ability of the agents of the present invention to suppress tumor growth in vivo.

For the formation of solid tumors, athymic mice can be injected with human or animal (e.g., mouse) cancerous cells such as those derived from breast cancer, ovarian cancer, prostate cancer or thyroid cancer, and following the formation of cancerous tumors the mice can be subjected to intra-tumor and/or systemic administration of an agent capable of downregulating PSMD1 expression level and/or activity.

The following cell lines (provided with their ATCC Accession numbers) can be used for each type of cancer model:

For breast cancer:

Human breast cancer cell lines—MDA-MB-453 (ATCC No. HTB-131), MDA-MB-231 (ATCC No. HTB-26), BT474 (ATCC No. HTB-20), MCF-7 (ATCC No. HTB-22), MDA-MB-468.

For ovarian cancer:

Human ovarian cancer cell lines—SKOV3 (ATCC No. HTB-77), OVCAR-3 HTB-161), OVCAR-4, OVCAR-5, OVCAR-8 and IGROV1;

For prostate cancer:

Human prostate cancer cell lines—DU-145 (ATCC No. HTB-81), PC-3 (ATCC No.CRL-1435);

For thyroid cancer:

Human derived thyroid cancer cell lines—FTC-133, K1, K2, NPA87, K5, WRO82-1, ARO89-1, DRO81-1;

For lung cancer:

Mouse lung carcinoma LL2 (LLC1) cells (Lewis lung carcinoma)—These cells are derived from a mouse bearing a tumor resulting from an implantation of primary Lewis lung carcinoma. The cells are tumorigenic in C57BL mice, express H-2b antigen and are widely used as a model for metastasis and for studying the mechanisms of cancer chemotherapeutic agents (Bertram J. S., et al., 1980, Cancer Lett. 11: 63-73; Sharma S., et al. 1999, J. Immunol. 163: 5020-5028).

For melanoma:

Mouse B16-F10 cells (Melanoma)—The cells are derived from mouse (C57BL/6J) bearing melanoma (Briles E. B., et al., 1978, J. Natl. Cancer Inst. 60: 1217-1222).

The cancerous cells can be cultured in a tissue culture medium such as the DMEM with 4 mM L-glutamine adjusted to contain 1.5 g/L sodium bicarbonate and 4.5 g/L glucose, supplemented with 10% fetal calf serum (FCS), according to known procedures (e.g., as described in the ATCC protocols).

Tumor formation in animal models by administration of cancerous cells—Athymic nu/nu mice (e.g., female mice) can be purchased from the Jackson Laboratory (Bar Harbor, Ma.). Tumors can be formed by subcutaneous (s.c.) injection of cancerous cells (e.g., $2\times10^6$ cells in 100 µl of PBS per mouse). Tumors are then allowed to grow in vivo for several days (e.g., 6-14 days) until they reach a detectable size of about 0.5 cm in diameter. It will be appreciated that injection of cancerous cells to an animal model can be at the organ from which the cell line is derived (e.g., mammary tissue for breast cancer, ovary for ovarian cancer) or can be injected at an irrelevant tissue such as the rear leg of the mouse.

To test the effect of the agents of the present invention on inhibition of tumor growth, the agents may be administered to the animal model bearing the tumor either locally at the site of tumor or systemically, by intravenous injection of infusion, via, e.g., the tail vein. The time of administration may vary from immediately following injection of the cancerous cell line (e.g., by systemic administration) or at predetermined time periods following the appearance of the solid tumor (e.g., to the site of tumor formation, every 3 days for 3-10 times as described in Ugen K. E. et al., Cancer Gene Ther. 2006 Jun. 9; [Epub ahead of print]).

Administration may be effected using a nucleic acid construct designed to express the active agent (e.g., a viral vector), naked pDNA and/or liposomes, as follows.

Tumor sizes are measured two to three times a week. Tumor volumes are calculated using the length and width of the tumor (in millimeters). The effect of the treatment can be evaluated by comparing the tumor volume using statistical analyses such as Student's t test. In addition, histological analyses can be performed using markers typical for each type of cancer.

According to one embodiment, the agents of the present invention are not formulated together with or co-administered with chemotherapeutic agents.

According to another embodiment, the agents of the present invention are co-administered or co-formulated with other known chemotherapeutic agents and/or anti-inflammatory agents. In addition, they may be administered with other known therapies, including but not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

Examples of other chemotherapeutic agents which may be co-delivered/coformulated with the agents of the present invention include but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

According to a particular agent, the additional chemotherapeutic agent is not a spindle poison. A spindle poison, also known as a spindle toxin, is a poison which disrupts cell division by affecting the protein threads which connect the centromere regions of chromosomes, known as spindles. Some spindle poisons include Mebendazole, Colchicine, Griseofulvin, Vinca Alkaloids and Paclitaxel (Taxol).

Examples of anti inflammatory drugs that can be administered in combination with the agent or polynucleotide encoding same include but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

It will be appreciated that since inhibition of PSMD-1 was shown to bring about death of cancerous cells, the present inventors also contemplate a method for screening for agents which are useful for treating a disease for which inhibiting a proteasome is advantageous. The method comprises:

(a) contacting the agent with a 26S proteasomal complex of a cell;

(b) analyzing an amount of dissociation of the 26S proteasomal complex into a 19S regulatory particle (RP) and a 20S subunit, wherein an upregulation of the dissociation and/or disassembly compared to an amount of dissociation and/or disassembly of the 26S proteasomal complex in an absence of the agent, is indicative of an agent useful for treating a disease for which inhibiting a proteasome is advantageous.

The 26S proteasomal complex may be in an isolated form or may be inside a cell population. According to one embodiment, the cells of the cell population are viable. According to another embodiment, the complex is located inside a protein extract.

Since the present inventors have shown that knock-down of PSMD1 (a protein of the 19S regulatory particle) enhances the dissociation of the 26S proteasomal complex, the method may be carried out by screening for agents which are capable of decreasing the level of the 19S regulatory particle and not the 20S subunit. More specifically, the method may be carried out by analyzing whether an agent is capable of down-regulating an amount of PSMD1 in the cell.

It will be appreciated that the amount or activity of PSMD1 (or any other protein in the 19S regulatory particle) may be analyzed on the protein level using method known in the art including but not limited to Western blot, radioimmunoassay, enzyme linked immunosorbent assay, FACs analysis and immunohistochemical analysis. The amount or activity of PSMD1 may be analyzed on the polynucleotide level using method known in the art including but not limited to Northern blot analysis, RT-PCR and microarray chips.

The candidate agents that may be tested as potential proteasome inhibitors according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

Following identification of a suitable agent it may be tested using additional assays such as the ones described herein above. Once therapeutic activity is confirmed, the agent may be synthesized in larger amounts for further testing and formulation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells -A Manual of Basic Technique" by Freshney, Wiley-Liss, New York (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Cells: MCF10A cells were cultured in DMEM:F12 medium with 5% horse serum (Gibco), 2 mM glutamine, 20 ng/ml epidermal growth factor, 10 µg/ml insulin, 0.5 mg/ml hydrocortisone, 100 ng/ml cholera toxin, 100 units/ml penicillin and 100 µg/ml streptomycin. OVCAR3 cells were cultured in RPMI medium (Gibco) with 15% FCS, 10 µg/ml insulin and the antibiotics as above. HEK 293T, NIH3T3 and MDA-MB-231 were cultured in DMEM and 8% FCS with antibiotics as mentioned above. All cells were maintained at 37° C. in a humidified incubator with 5.6% $CO_2$.

Plasmids and viral production: A lentiviral Tet-inducible TRIPZ vector with shRNAmir against 26S proteasome subunit Psmd1 was purchased from Open Biosystems (Thermo Scientific) and used to down regulate 26S levels in MCF-10A, MDA-MB-231, SK-OV-3 and OVCAR3 cells. Transducing lentiviral particles were produced in HEK 293T cells according to the manufacturer's protocol. Cell lines were selected with 2 µg/ml puromycin or left non-selected before subjection to experiments.

Production of retrovirus particles was performed by transducing HEK 293T cells with either pBabe empty or pBabe H-Ras V12 and psi helper plasmid by the calcium phosphate method for the NIH3T3 infection or by transduction with retroviral pBabe H-Ras V12 vector or an empty vector into the Phoenix packaging cell line that was used for retrovirus production. The MCF10A cells were subsequently infected with retroviral particles when the cultures were 60-80% confluent and allowed to recover for 24 h after infection before antibiotic selection in media containing puromycin.

Induction of Psmd1 knockdown and reduction in the 26S proteasomal complexes: Cells of interest were infected with the lentivirus particles (infections conditions vary between cell lines). Selection with puromycin was employed for a week (the concentration has to be determined based on the cell type). To induce the knockdown, the cells were treated with doxycycline between 0.5-1.5 mg/ml. A reduction of the 26S proteasomal complex was observed after 48 hours (see FIG. 2). The efficiency of the reduction in the 26S proteasomal complex can be analyzed by subjecting the cellular extract to nondenaturing PAGE as previously described (28).

This enables visualization of the reduction in the 26S proteasomal complex and not only the subunit expression on the protein level (as examined by the SDS-PAGE).

Flow cytometry: Cells were seeded at a density of $5\times10^5$ per 9 cm dish and Psmd1 knockdown was induced by the addition of doxycycline (1 µg/ml) in the presence of puromycin (2 µg/ml). After 96 hours, floating and attached cells were collected and combined together, washed twice with PBS and fixed in 70% ethanol. The cells were further washed with PBS and resuspended in 50 µg/ml RNase A and 25 µg/ml propidium iodide in PBS. In each assay, triplicates of 30,000-50,000 cells were collected by LSRII instrument and analyzed with the BD FACSDiva software (BD Biosciences).

Cell proliferation: Cells ($2\times10^3$) were seeded in a well of 96-well plate in the presence of puromycin (2 µg/ml) with or without doxycycline (1 µg/ml). Cell proliferation was analyzed using the XTT assay (Biological Industries) and spectrophotometrically quantified. The results obtained by the XTT assay were confirmed by direct counting of cells over the period of Psmd1 KD induction.

In the recovery experiment, MDA-MB-231 cells ($2\times10^3$) were seeded in a well of 96-well plate in the presence of puromycin (2 µg/ml) and doxycycline (1 µg/ml). After 72 hours, the cells were washed twice with the culture medium and supplemented with fresh medium with puromycin but without doxycycline for an additional seven days. The ability of cells to recover from Psmd1 KD was compared to growth characteristics of cells that continued to be supplemented with 1 µg/ml doxycycline after the washing step or were not induced at all.

Anchorage-independent growth: Cells ($3\times10^4$) were added to 0.5 ml of growth medium with 0.3% low-melting point agar (BioRad) and layered onto 0.5 ml of 0.5% agar beds in twelve-well plates in the presence of puromycin (2 µg/ml) with or without doxycycline (1 µg/ml). Colonies were photographed after one week.

Colony formation assay: Cells were seeded at a density of 30 cells/cm$^2$ and cultured in the presence of puromycin (2 µg/ml) with or without doxycycline (1 µg/ml) for 14 days. Colonies were fixed with 70% isopropanol for 10 minutes followed by staining with 0.1% crystal violet.

Protein extraction and immunoblot analysis: Cells were collected and lysed in RIPA buffer containing (50 m Tris-HCl, pH 8, 150 mM NaCl, 1% Nonidet P-40 (v/v), 0.5% deoxycholate (v/v), 0.1% SDS (v/v), 1mM DTT and Sigma protease inhibitor mixture (P8340) diluted 1:100) as previously described (29), the extract was subjected to ultracentrifugation (13,000 g, 15min) and the supernatant was used as the protein extract. Protein concentrations were determined by Bradford assay (Bio-Rad) and equal amount was mixed with Laemmli sample buffer [4% SDS, 20% glycerol, 10% 2-mercaptoethanol and 0.125M Tris-HCl], heated at 95° C. for 5 minutes and loaded on a 10% polyacrylamide-SDS gel. Following electrophoresis, proteins were transferred to cellulose nitrate 0.45 mm membranes (Schleicher & Schuell). The antibodies used were: Rabbit anti PSMA4, PSMD1 (Acris), Fibronectin, mouse anti c-Myc, c-Jun (Santa-Cruz), Goat anti NQO1 C19 R20 (Santa-cruz), anti-Hsc-70(14-16) (30), Mouse anti Actin (Sigma) RNR-R2 (Santa-Cruz). Anti p53 (1801), anti p21 (Santa-Cruz). Secondary antibodies were HRP-linked Goat anti-mouse and Rabbit (Jackson ImmunoResearch). Signals were detected using the Ez-ECL kit (Biological Industries). And detected by ImageQuant LAS 4000 (GE).

Nondenaturing PAGE: Proteasomal samples were loaded on a nondenaturing 4% polyacrylamide gel using the protocol previously described (28, 31). Gels were either overlaid with Suc-LLVY-AMC (50 µM) for assessment of proteasomal activity by ImageQuant LAS 4000 (GE) or transferred to nitrocellulose membranes where immunoblotting with anti PSMA4 antibody was conducted.

Example 1

H-Ras V12 Transformation Induces Elevation in the 26S Proteasomal Complex

Cancer cells exhibit high proteasomal activity (25, 32) but its mechanism has not been resolved. The present inventors examined the possibility that the observed high proteasome activity is the result of an increase at the 26S proteasome level. To this end NIH3T3 cells were transformed by H-Ras V12 active mutant oncogene. The cells displayed a spindle-shaped and highly refractile morphology, with long protrusions and grew in a disorganized fashion with few cell-cell interactions, possibly reflecting a reorganization of the cytoskeleton (FIG. 1A). Remarkably, the transformed cells contained higher levels of the 26S proteasome both at the level of immunoblot assessment and activity (FIG. 1B). The observed increase at the level of the proteasome is not the result of an increase at the level of subunit expression (FIG. 1C). Similar results were obtained with H-Ras transformation of MCF10A cells (see below). These data suggest that in H-Ras transformed cells the 26S proteasome complex is either more stable or more efficiently assembled.

Example 2

Selective Down Regulation of the 26S Proteasome Complex

The observation that the level of the 26S proteasomes is increased in the transformation process led the present inventors to hypothesize that the actual level of this complex is critical for the transformation to take place and therefore specific inhibition of the 26S proteasomal complex could be utilized to selectively block/kill transformed cells. Currently there are no specific inhibitors of the 26S proteasome that allow proper functioning of the 20S proteasome. Keeping active 20S proteasome is important given the findings that 20S proteasome is functional in the cells as well. Given these considerations it was decided to down-regulate the 26S proteasome by the knockdown of the 19S regulatory complex. The present inventors chose to knockdown PSMD1 one of the subunits of the 19S complex unique to the 26S proteasome (FIG. 2A). To this end, lentiviral vectors were utilized with shRNAmir against human 26S proteasome subunit Psmd1 and control shRNAmir. To be able to control the expression of PSDM1-shRNAmir a pTRIPZ lentivirus shRNAmir was utilized which is a tetracycline inducible knockdown vector (Open Biosystems, clone number V2THS_170797 Sense-CTCATATTGGGAATGCTTA (SEQ ID NO: 1) antisense-TAAGCATTCCCAATATGAG (SEQ ID NO: 2). The full length sequence is set forth in SEQ ID NO: 3 TGCTGTTGACAGTGAGCGAGCTCATAT-TGGGAATGCTTATTAGTGAAGCCACAGATG-TAATAAGCATTCCCAATATGAGCCTGCCTACTGC-CTCGGA.

Transducing lentivirus particles were produced according to the manufacturer's protocol. MCF10A, an immortalized, non-transformed epithelial cell line derived from human fibrocystic mammary tissue was utilized. These cells are near diploid and as such considered normal human mammary epithelial cells (33). Utilization of human cells is essential since the present strategy knocks down specifically human Psmd1. Knocking down the Psmd1 (Rpn2) subunit resulted in a sharp reduction of Psmd1 but not of the control Psmd4 (FIG. 2B). Remarkably, Psmd1 knockdown was sufficient to markedly decrease the level of the 26S proteasome (FIG. 2C) suggesting that the level of the 26S complex can be artificially modulated.

Example 3

Down Regulation of 26S Complex in H-Ras Transformed Cells

Naive MCF10A cells were infected with the viral vector encoding a doxycycline-induced shRNAmir that targets the Psmd1 proteasomal subunit. Expression of the Psmd1 shRNA was induced by the addition of doxycycline to the medium for 48 hours. MCF10A stably expressing the Psmd1 shRNA were further transduced with a viral vector expressing the H-Ras V12 active transforming mutant (FIG. 3A). Following the transformation process, the level of Psmd1 increased dramatically (FIG. 3B). Fibronectin a marker of epithelial mesenchymal transition (EMT) and transformation in MCF10A cells was also increased. Interestingly, upon addition of doxycycline to the medium for 72 hours a sharp reduction in the level of Psmd1 was obtained. Also, under these conditions a sharp reduction at the level of fibronectin was revealed, whereas the level of some key regulatory proteins was increased. These proteins have been previously shown to be increased following proteasomal inhibition and may be involved in cellular apoptosis such as Myc (34, 35) and c-Jun (36). Next, 26S activity was measured in a native gel. It was found that in the H-Ras transformed cells there are higher levels of the 26S proteasomes (FIG. 3C). Remarkably, the levels of the functional 26S proteasomal complexes significantly decreased in the control and H-Ras transformed MCF10A cells following addition of doxycycline. These data suggest that the 26S complex in the transformed cells can be down regulated by the present experimental strategy.

Example 4

H-Ras Transformed Cells are Highly Sensitive to 26S KD

Having demonstrated that the level of the 26S complex is down-regulated in the H-Ras V12 transformed cells, the present inventors next examined the growth rates of the control MCF10A and H-Ras V12 transformed cells following 26S knock-down. In the control MCF10A cells, although the 26S knockdown exhibited a certain lag in growth, the knockdown did not inhibit cell growth (FIG. 4A). Remarkably, the H-Ras V12 transformed cells on the other hand were very sensitive to 26S knockdown and stopped proliferating (FIG. 4B). Unlike the control cells, the Ras-transformed cells lost the epithelial cell morphology, as analyzed by microscopy and exhibited a highly refractile, fibroblastic morphology and growth in a disorganized fashion (FIG. 4C). Examining the cellular morphology of MCF10A cells revealed that the effect of the 26S KD is specifically evident in the H-Ras V12 transformed MCF10A. FACS analysis revealed that the rate of cell death, as quantified by the level of the sub-G1 fraction, is about twice higher in the 26S knockdown MCF10A cells that are H-Ras V12 transformed (FIG. 4D).

Transformed cells, in addition to loss of contact inhibition (cells can grow over one another) acquire anchorage independence capacity (cells form colonies in soft agar). Growth in soft agar is considered the most stringent assay for detecting malignant transformation of cells. Accordingly, the present inventors examined the colony formation capacity of the 26S knockdown cells in soft agar. In contrast to the H-Ras V12 transformed MCF10A cells that formed colonies, the 26S knock-down transformed cells did not grow under this condition (FIG. 4E). These results suggest that 26S KD preferentially and efficiently inhibits growth of transformed cells.

Example 5

Drug Resistant MBA-MD-231 Breast Cancer Cells are Highly Sensitive to 26S KD

In breast cancer, approximately 10-20% of the cases are considered triple negative breast cancer (TNBC) as they lack or express at low levels the three receptors; estrogen, progesterone and Her2 (37). These cancers have lower prognosis, and show resistance to many commonly used therapies including endocrine therapies, HER2 targeting drugs and in some cases standard chemotherapy (38, 39). The MBA-MD-231 are TNBC cells that can serve as a good in vitro model for aggressive tumors that are resistant to most currently available breast cancer drugs (38, 39). The present inventors examined the ability of MBA-MD-231 cells to proliferate following the induction of 26S knockdown and compared it to MCF10 a non-transformed cell line. Both lines were stably transduced with the lenti-vector expressing Psmd1 shRNA under the Tet on promoter. Induction of 26S knockdown by doxycycline addition in cells completely inhibited MBA-MD-231 proliferation (FIG. 5A) whereas the growth of the control MCF10 cells displayed biphasic growth cure (FIG. 5B). The early phase, (up to 5 days), of growth was retarded, but later normal growth rate was resumed (see also FIG. 4A), suggesting that the effect on non-tumorgenic breast epithelial cells was transient.

Light microscopy visualization revealed that 72 hours after induction of Psmd1 shRNA expression, MDA-MB-231 cells lost their normal morphology and appeared as cell aggregates (FIG. 5C). This type of cell aggregation may indicate that the cells undergo excessive death. To examine cell death a FACS analysis was conducted to quantify the subG1 apoptotic fraction. As a control, the same experimental conditions were employed on the MCF10A cells. The subG1 population was about 50% in MDA-MB-231 cells, which is two fold higher than the level obtained with the MCF10A cells. Finally Western blot analysis not only validated a reduction in the Psmd1 protein level, but also in the proliferating marker such as RNR-R2 enzyme and an increase in the level of the cell cycle growth inhibitor p21 (FIG. 5F). These data suggest that the drug resistant MDA-MB-231 cells are extremely sensitive to 26S KD.

Example 6

Transient Psmd1 Knockdown is Sufficient to Induce MDA-MB-231 Cell Death

Figure 6:
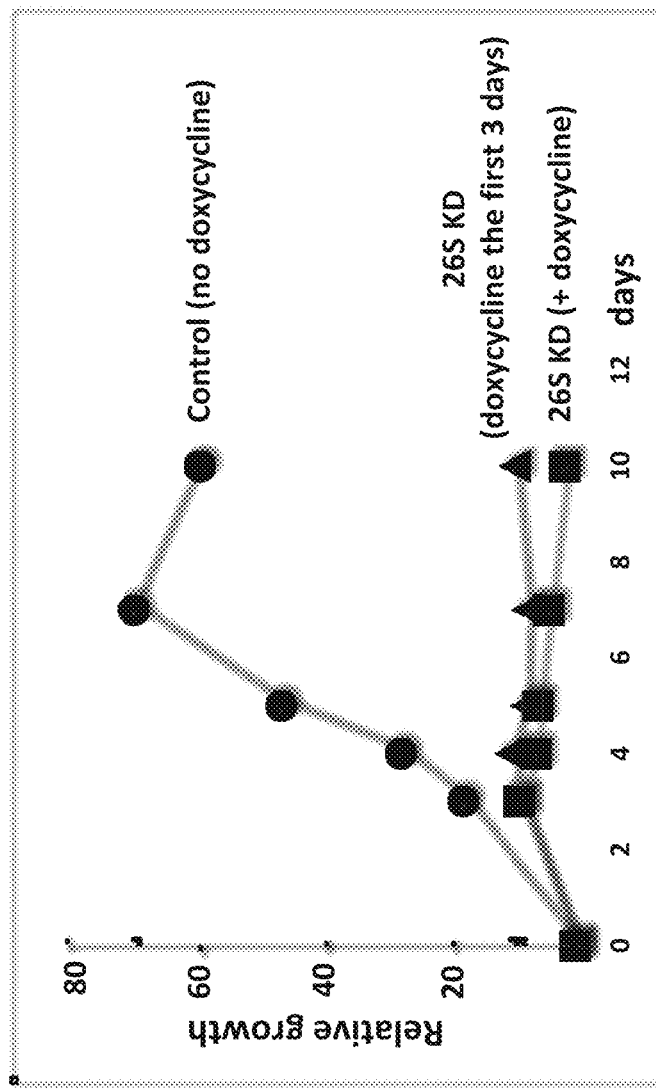
FIG. 6 illustrates that transient Psmd1 knockdown is sufficient to induce MDA-MB-231 cell death. MDA-MB-231 stably expressing the doxycycline-induced knockdown of Psmd1 shRNA was incubated for 72 hours in the presence or absence (control) of 1 µg/ml doxy for the induction of Psmd1 knockdown. After 72 hours the doxycycline was either removed or kept to follow cell proliferation rate for additional 7 days.

Two models may explain the finding that MCF10A cells, but not MDA-MB-231 cells, recovered from 26S knockdown in only a few days. One that Psmd1 shRNA effect is transient but cell fate to survive (MCF10A) or to die (MDA-MB-231 cells) is determined at this early stage, and the other that only the normal cells have the capacity to recover from the 26S KD after initial stress. To address these possibilities expression of Psmd1 shRNA was induced for only a short period by removing the inducer doxycycline. After 3 days of induction of Psmd1 knockdown with doxycycline in MDA-MB-231, cells were washed and medium devoid of doxycycline was added. The cells that transiently expressed Psmd1 knockdown (26S KD) were compared to the stably expressing Psmd1 KD and control (FIG. 6). Strikingly, the transient expression of Psmd1 KD was sufficient to inhibit cell growth and the cells did not show any recovery during the time frame analyzed (10 days). These data suggest that the entry of the MDA-MB-231 cells into a death program is irreversible and is dictated very early after 26S knockdown induction.

Example 7

Drug Resistant OVCAR-3 Cells are Highly Sensitive to 26S KD

To confirm the finding that aggressive and drug resistant tumor cell lines are more prone to death under 26S knockdown, ovarian cancer cells were used. The OVCAR-3 cell line are resistant to clinically relevant concentrations of adriamycin, melphalan and cisplatin making the OVCAR-3 an appropriate in vitro model system to study drug resistance in ovarian cancer (40, 41). OVCAR-3 line was established from the malignant ascites of a patient with progressive adenocarcinoma of the ovary. The cells form colonies in soft agar and have an abnormal karyotype. It has been shown that HBX8/Rsf1 gene is amplified in this aggressive ovarian cancer cells (42). Another interesting cell line is SK-OV-3 that was derived from the ascitic fluid from a 64 year old Caucasian female with an ovarian tumor. SK-OV-3 cells are resistant to tumor necrosis factor and to several cytotoxic drugs including diphtheria toxin, cis-platinum and adriamycin, forms moderately well differentiated adenocarcinoma consistent with ovarian primary cells. The HBX8/Rsf1 gene is not amplified in this lower grade ovarian cancer cells, but upon forced expression of HBX8/Rsf1 the cells become more aggressive (43).

Figures 7A, 7B, 7C:
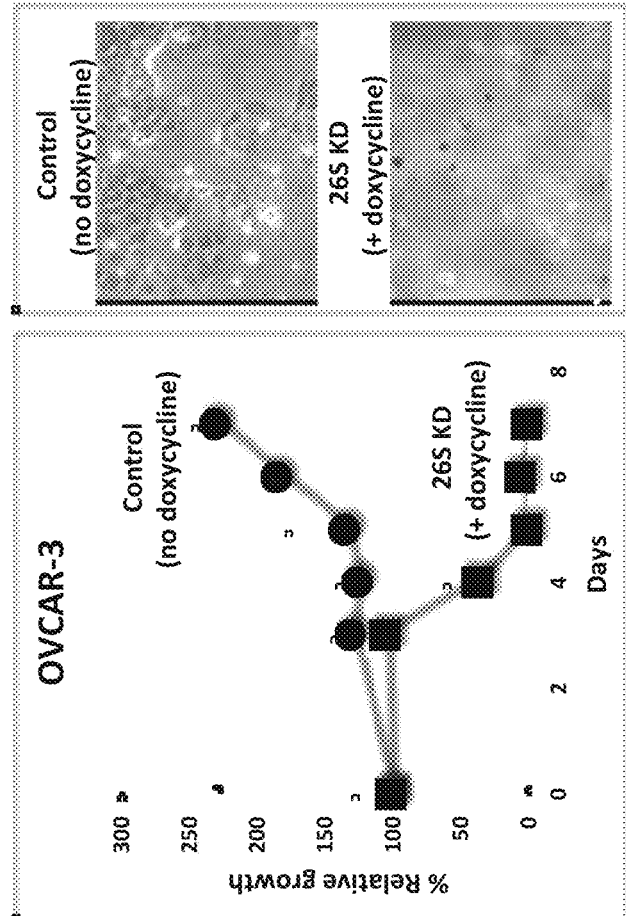
FIGS. 7A-7C illustrate that OVCAR-3 cells are highly sensitive to Psmd1 knockdown. A. SK-OV-3 cells transduced with the lentivector expressing Psmd1 shRNA under doxycycline induction was established and its rate of proliferation was followed for 8 days in the presence or absence of doxycycline. B. OVCAR-3 cells were used to follow the effect of Psmd1 knockdown on its growth rate as described in panel A. C. Microscopy pictures of the treated cells are shown.

SK-OV-3 and OVCAR-3 cell lines were infected with the viral vector containing Psmd1 shRNA under Tet on promoter. Induction of the Psmd1 knockdown by doxycycline treatment resulted in partial death of SK-OV-3 cell line (FIG. 7A), whereas OVCAR-3 growth was blocked and cells died after 3 days (FIG. 7B). Light microscopy confirmed that only a few cells with apoptotic appearance are found in the culture (FIG. 7C). These data suggest that the aggressive drug resistant ovarian cancer cells are very sensitive to 26S KD.

Example 8

PSMD1 Knockdown Inhibits Tumor Formation in Nude Mice

Control (naïve) OVCAR-3 cells or stably positive to inducible Psmd1 shRNA expressing lentivirus were established. $1.3 \times 10^6$ cells were injected subcutaneously (sc) into the bilateral subscapular areas of nude athymic BALB/c mice. The left side was injected with the control cells whereas the right side with the PSMD1 shRNA positive cells. 10 mice were injected and divided into 2 groups. One group was given 3% sucrose in the water and the other 3% sucrose with 2 mg/ml of doxycycline in the water. The water was changed every 3 days. After 6 weeks the tumor size was analyzed.

Results

The results are summarized in Table 1, herein below.

TABLE 1

| OVCAR-3 | 26S KD OVCAR-3 |
|---|---|
| 1.353 cm³ | 0.000 cm³ |
| 0.905 cm³ | 0.000 cm³ |
| 0.103 cm³ | 0.000 cm³ |
| 0.000 cm³ | 0.000 cm³ |
| 0.564 cm³ | 0.000 cm³ |

The table shows that in the 26S KD cells no tumor developed in doxycycline treated cells whereas the naïve OVCAR-3 developed into large tumors in 4 out of 5 mice.

Example 9

Sensitivity of Human Colorectal Cancer Cell Line (HCT116) or Human non Small Cell Lung Carcinoma (H1299) to Rpn2 shRNA Human colorectal cancer cell line (HCT116) or human non-small cell lung carcinoma (H1299) were seeded on 96 well plates (1000 cells per well) and were induced to express Rpn2 shRNA (26S KD) by 1 mg/ml of doxycycline. Cell growth over time was evaluated by XTT assay.

Results

The number of cells was counted both in the presence and the absence of the shRNA. The results are provided in FIGS. 8A-B.

Example 10

PSMD1 Knockdown Kills Cancer Cells from Different Origins

In this example, the present inventors examined whether downregulation of PSMD1 is effective against carcinoma cells. To this end, the osteocarcinoma cell line, U2OS was used.

Results

Figures 9A, 9B:
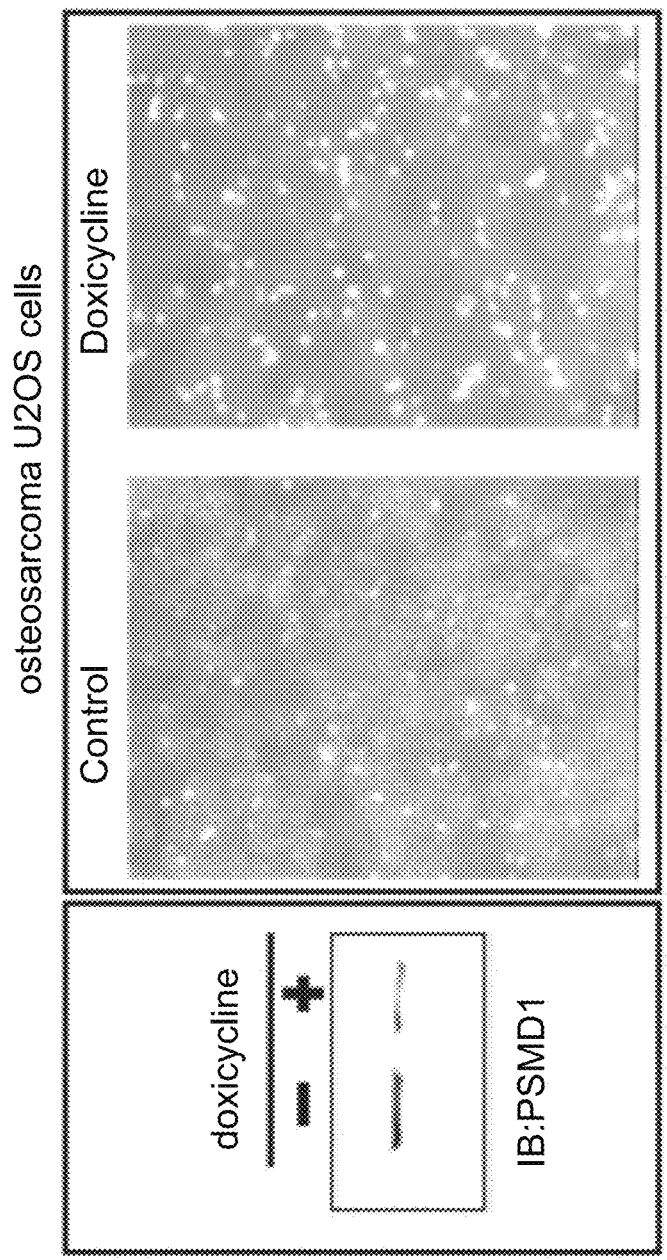
FIGS. 9A-9B illustrate that PSMD1 knockdown kills carcinoma cancer cells. U2OS, osteocarcinoma cells, were infected with lentivirus vector encoding the PSMD1 shRNA under doxycycline induction. A. under doxycycline induction the level of PSMD1 was reduced. B. After 5 days cells induced by doxycycline were mostly dead, as microscopically visualized.
Figure 10:
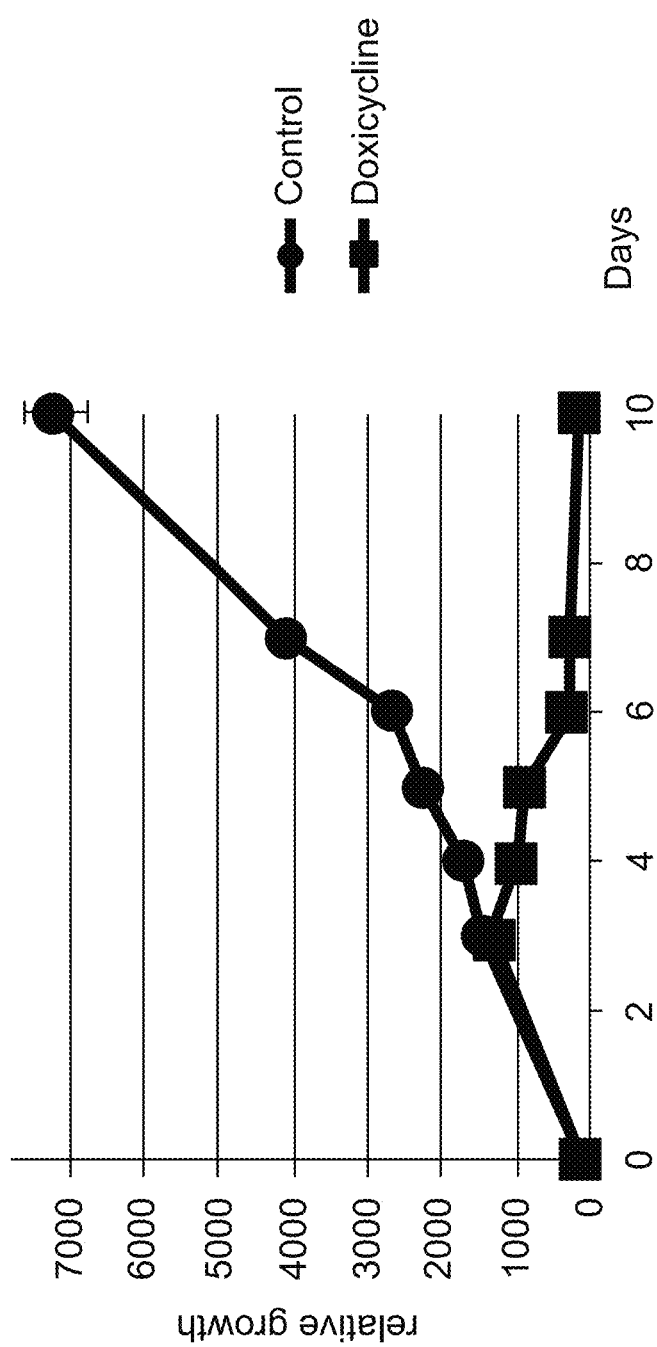
FIG. 10 As tested by XTT, induction of PSMD1 expression by doxycycline killed essentially all the cells following 6 days.

The data presented in FIG. 9 and FIG. 10 illustrates that this cell line is highly susceptible to 26S proteasomal disassembly and is easily killed following reduction of PSMD1.

Example 11

PSMD1 Knockdown Kills Cancer Cells that are p53 Negative as Well

The tumor suppressor p53 gene is often mutated in many cancers. Therefore it was important to show that the present approach is effective against tumor cells that are 53 positive.

Results

The data presented in the FIG. 8 show that PSMD1 knockdown is effective regardless of p53 status.

Example 12

19S Disassembly Leads to Cancer Cell Killing

To validate the assumption that the killing is mediated by 19S disassembly and not by PSMD1, 2 other components of the 19S particle were knocked down, namely PSMD 11 (also named Rpn6) and PSMD 6 (Rpn7), using shRNAs.

PSMD6:
Vector: pLKO.1 (Sigma)
TRC number:TRCN0000143904
Clone ID: NM_014814.1-1019s1c1
Sequence:

```
                                              (SEQ ID NO: 18)
CCGGCAGGAACTGTCCAGGTTTATTCTCGAGAATAAACCTGGACAGTTC

CTGTTTTTG
```

TRC number:TRCN0000145517
Clone ID: NM_014814.1-946s1c1
Sequence:

```
                                              (SEQ ID NO: 19)
CCGGGCTGGAATCATATAGGTCATTCTCGAGAATGACCTATATGATTCC

AGCTTTTTG
```

PSMD11:
Vector: pLKO.1 (Sigma)
TRC number: TRCN0000272509
Clone ID: NM_002815.2-670s21c1
Sequence:

```
                                              (SEQ ID NO: 20)
CCGGGGACATGCAGTCGGGTATTATCTCGAGATAATACCCGACTGCATG

TCCTTTTTG
```

TRC number: TRCN0000003950
Clone ID: NM_002815.x-1116s1c1
Sequence:

```
                                              (SEQ ID NO: 21)
CCGGCCGACGTGGAAAGGAAATTATCTCGAGATAATTTCCTTTCCACGT

CGGTTTTT
```

Results

Figure 11:
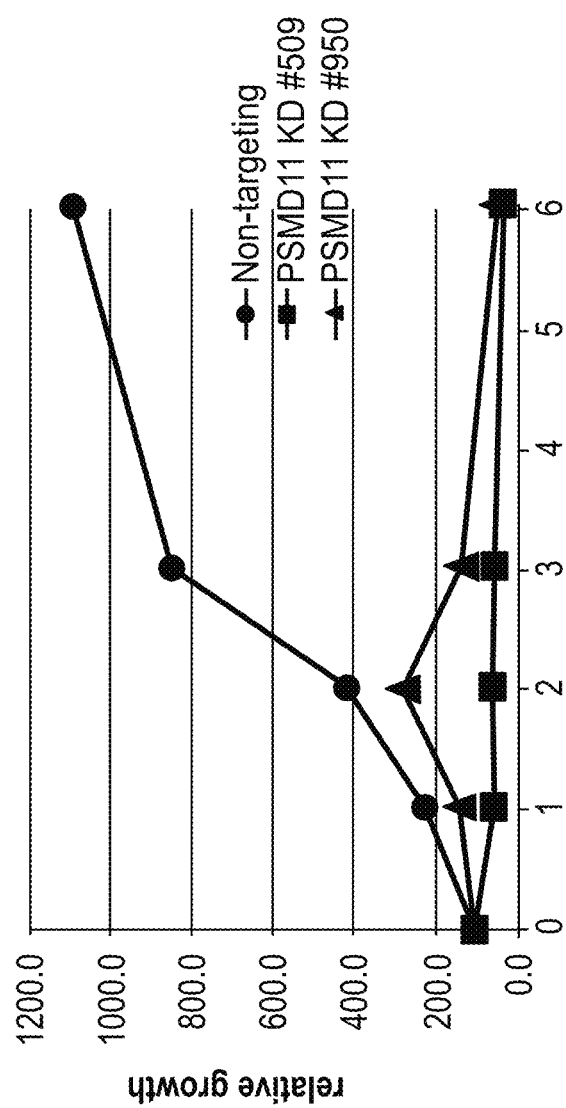
FIG. 11 is a graph illustrating that PSMD11 (also named Rpn 6) knockdown kills cancer cells. Two lentivectors each expressing a different shRNA that targeted against PSMD11 were tested. Both were as effective in cancer cell (HCT116) killing as PSDM1 shRNA. In this experiment shRNA was expressed directly without doxycycline induction.
Figure 12:
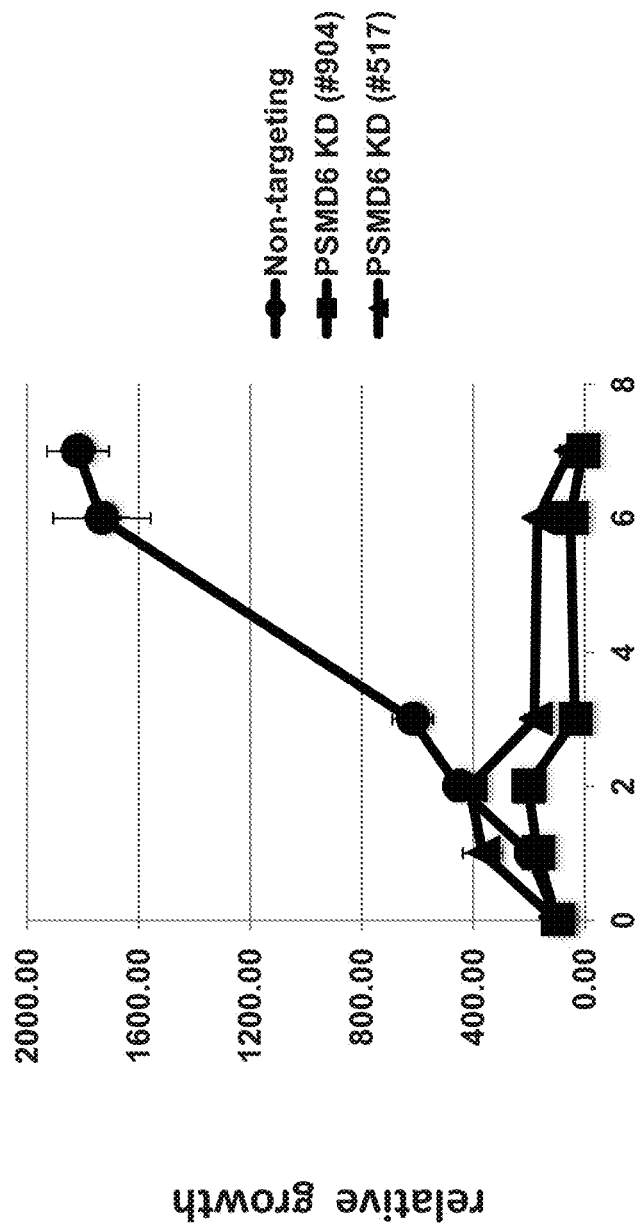
FIG. 12 is a graph illustrating that PSMD6 (also named Rpn 7) knockdown kills HCT116 cancer cells.
Figure 14:
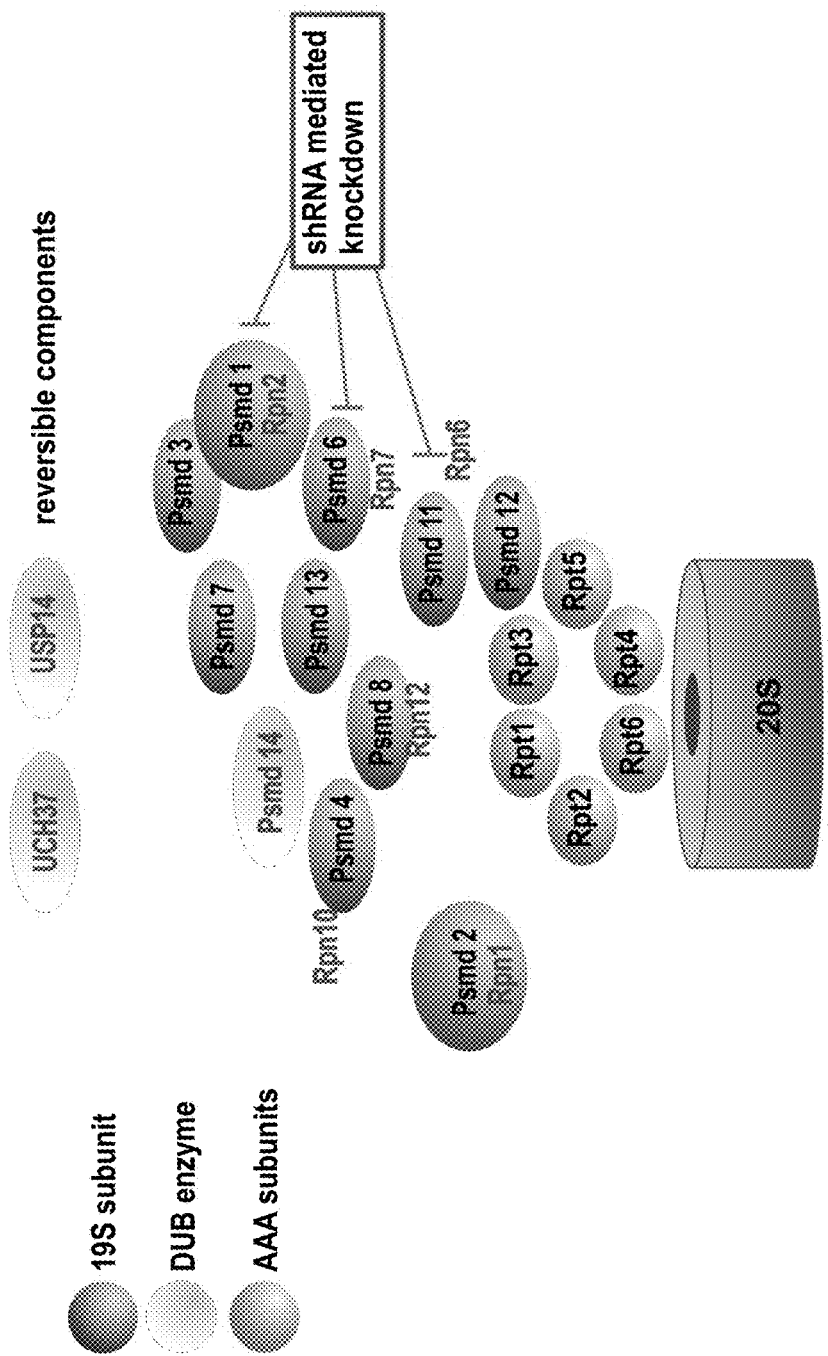
FIG. 14 is a scheme showing the different targets of the 19S particle that were targeted in order to kill cancer cells.

Both knockdown of Rpn6 and Rpn7 were as effective as PSMD1 knockdown in killing cancer cells (FIGS. 11 and 12). These data suggest that 19S disassembly is important in killing the cancer cells. The different 19S particle components that were targeted are presented in FIG. 14.

Example 13

Psmd1 shRNA Lentivector in Cancer Therapy

Nude mice were injected subcutaneously (sc) with $3 \times 10^6$ HCT 116 cells in 3 groups (A,B,C) each of 5 mice (Table 2). Group A was not infected with a virus. For group B, the HCT116 cells were co-injected with the Psmd1 shRNA lentivector (not inducible). For group C, the Psmd1 shRNA lentivector was injected 7 days following the injection of the cells.

Results

The results are summarized in Table 2, herein below.

TABLE 2

| Mouse # | A<br>Not infected but cell injected* | B<br>Infected** at time zero of cell injection | C<br>Infected 7 days after cell injection |
|---|---|---|---|
| 1 | 2.40*** | 0.00 | 0.72 |
| 2 | 2.10 | 0.00 | 0.90 |
| 3 | 0.42 | 0.00 | 0.00 |
| 4 | 0.00 | 0.00 | 0.00 |
| 5 | 0.00 | 0.00 | 0.00 |

*$3 \times 10^6$ cells in 0.1 ml injected SC
**lentivirus coding Psmd1 shRNA produced in HEK293T cells
***tumor size in $cm^3$ Example 14

Downregulation of Psmd6 Results in the Disassembly of the 26S Proteasome

Downregulation of Psmd6 was effected using the shRNAs (SEQ ID NO: 18 and 19). The amount of proteasome subunits was measured by Western blot. In order to analyze the amount of 20S subunit, an antibody that detected the alpha4 subunit of the 20S proteaseome (Psma4) was used. Activity of the proteasomes in the gel was determined by the cleavage of the Suc-LLVY-AMC peptide (Glickman, M. H., Rubin, D. M., Fried, V. A., and Finley, D. (1998) Mol Cell Biol 18(6), 3149-3162).

Results

Figure 13:
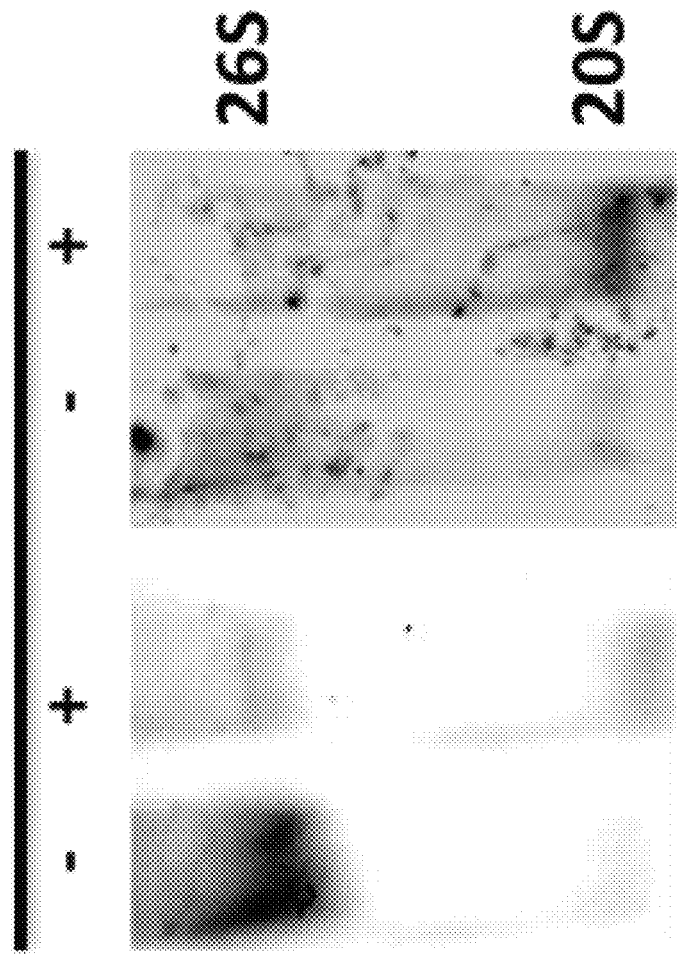
FIG. 13 is a photograph showing the results of Western blot analysis. The results show that downregulation of Psmd6 results in the decrease of the 26S proteasome subunit with the concurrent increase in the 20S subunit.

As can be seen from FIG. 13, downregulation of PSmd6 resulted in a decrease in 26S activity and amount and an increase in the amount of 20S.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFRENCES

1. Coux O, Tanaka K, Goldberg A L. Structure and functions of the 20S and 26S proteasomes. Annu Rev Biochem 1996; 65: 801-47.
2. Zwickl P, Voges D, Baumeister W. The proteasome: a macromolecular assembly designed for controlled proteolysis. Philos Trans R Soc Lond B Biol Sci 1999; 354: 1501-11.
3. Hershko A, Ciechanover A. The ubiquitin system. Annu Rev Biochem 1998; 67: 425-79.

4. Varshavsky A. The ubiquitin system. Trends Biochem Sci 1997; 22: 383-7.
5. Smith D M, Kafri G, Cheng Y, Ng D, Walz T, Goldberg A L ATP binding to PAN or the 26S ATPases causes association with the 20S proteasome, gate opening, and translocation of unfolded proteins. Mol Cell 2005; 20: 687-98.
6. Navon A, Goldberg A L Proteins are unfolded on the surface of the ATPase ring before transport into the proteasome. Mol Cell 2001; 8: 1339-49.
7. Hochstrasser M. Ubiquitin-dependent protein degradation. Annu Rev Genet 1996; 30: 405-39.
8. Tsvetkov P, Reuven N, Prives C, Shaul Y. The susceptibility of the p53 unstructured N-terminus to 20S proteasomal degradation programs stress response. J Biol Chem 2009.
9. Wiggins C M, Tsvetkov P, Johnson M, et al. BIMEL, an intrinsically disordered protein, is degraded by 20S proteasomes in the absence of poly-ubiquitylation. J Cell Sci; 124: 969-77.
10. Adler J, Reuven N, Kahana C, Shaul Y. c-Fos Proteasomal Degradation by Default and its Regulation by NQO1 Determines c-Fos Serum Response Kinetics. Mol Cell Biol.
11. Shaul Y, Tsvetkov P, Reuven N. IDPs and Protein Degradation in the Cell: John Wiley & Sons, Inc.; 2010.
12. Asher G, Reuven N, Shaul Y. 20S proteasomes and protein degradation "by default". Bioessays 2006; 28: 844-9.
13. Mao I, Liu J, Li X, Luo H. REGgamma, a proteasome activator and beyond? Cell Mol Life Sci 2008; 65: 3971-80.
14. Hoeller D, Dikic I. Targeting the ubiquitin system in cancer therapy. Nature 2009; 458: 438-44.
15. Bedford L, Lowe J, Dick L R, Mayer R J, Brownell J E. Ubiquitin-like protein conjugation and the ubiquitin-proteasome system as drug targets. Nat Rev Drug Discov; 10: 29-46.
16. Navon A, Ciechanover A. The 26 S proteasome: from basic mechanisms to drug targeting. J Biol Chem 2009; 284: 33713-8.
17. Arlt A, Bauer I, Schafmayer C, et al. Increased proteasome subunit protein expression and proteasome activity in colon cancer relate to an enhanced activation of nuclear factor E2-related factor 2 (Nrf2). Oncogene 2009; 28: 3983-96.
18. Chen L, Madura K. Increased proteasome activity, ubiquitin-conjugating enzymes, and eEF1A translation factor detected in breast cancer tissue. Cancer Res 2005; 65: 5599-606.
19. Wyke S M, Russell S T, Tisdale M J. Induction of proteasome expression in skeletal muscle is attenuated by inhibitors of NF-kappaB activation. Br J Cancer 2004; 91: 1742-50.
20. Adams J, Kauffman M. Development of the proteasome inhibitor Velcade (Bortezomib). Cancer Invest 2004; 22: 304-11.
21. Richardson P G, Barlogie B, Berenson J, et al. A phase 2 study of bortezomib in relapsed, refractory myeloma. N Engl J Med 2003; 348: 2609-17.
22. Hideshima T, Richardson P, Chauhan D, et al. The proteasome inhibitor PS-341 inhibits growth, induces apoptosis, and overcomes drug resistance in human multiple myeloma cells. Cancer Res 2001; 61: 3071-6.
23. Chauhan D, Catley L, Li G, et al. A novel orally active proteasome inhibitor induces apoptosis in multiple myeloma cells with mechanisms distinct from Bortezomib. Cancer Cell 2005; 8: 407-19.
24. Caravita T, de Fabritiis P, Palumbo A, Amadori S, Boccadoro M. Bortezomib: efficacy comparisons in solid tumors and hematologic malignancies. Nat Clin Pract Oncol 2006; 3: 374-87.
25. Adams J, Palombella V J, Sausville E A, et al. Proteasome inhibitors: a novel class of potent and effective antitumor agents. Cancer Res 1999; 59: 2615-22.
26. Rajkumar S V, Richardson P G, Hideshima T, Anderson K C Proteasome inhibition as a novel therapeutic target in human cancer. J Clin Oncol 2005; 23: 630-9.
27. Voorhees P M, Orlowski R Z. The proteasome and proteasome inhibitors in cancer therapy. Annu Rev Pharmacol Toxicol 2006; 46: 189-213.
28. Elsasser S, Schmidt M, Finley D. Characterization of the proteasome using native gel electrophoresis. Methods Enzymol 2005; 398: 353-63.
29. Tsvetkov P, Adamovich Y, Elliott E, Shaul Y. E3 ligase STUB1/CHIP regulates NAD(P)H:quinone oxidoreductase 1 (NQO1) accumulation in aged brain, a process impaired in certain Alzheimer disease patients. J Biol Chem; 286: 8839-45.
30. Elliott E, Tsvetkov P, Ginzburg I. BAG-1 associates with Hsc70.Tau complex and regulates the proteasomal degradation of Tau protein. J Biol Chem 2007; 282: 37276-84.
31. Glickman M H, Rubin D M, Fried V A, Finley D. The regulatory particle of the Saccharomyces cerevisiae proteasome. Mol Cell Biol 1998; 18: 3149-62.
32. Schwartz A L, Ciechanover A. Targeting proteins for destruction by the ubiquitin system: implications for human pathobiology. Annu Rev Pharmacol Toxicol 2009; 49: 73-96.
33. Soule H D, Maloney T M, Wolman S R, et al. Isolation and characterization of a spontaneously immortalized human breast epithelial cell line, MCF-10. Cancer Res 1990; 50: 6075-86.
34. Tani E, Kitagawa H, Ikemoto H, Matsumoto T. Proteasome inhibitors induce Fas-mediated apoptosis by c-Myc accumulation and subsequent induction of FasL message in human glioma cells. FEBS Lett 2001; 504: 53-8.
35. Gregory M A, Hann S R. c-Myc proteolysis by the ubiquitin-proteasome pathway: stabilization of c-Myc in Burkitt's lymphoma cells. Mol Cell Biol 2000; 20: 2423-35.
36. Yang Y, Ikezoe T, Saito T, Kobayashi M, Koeffler H P, Taguchi H. Proteasome inhibitor PS-341 induces growth arrest and apoptosis of non-small cell lung cancer cells via the JNK/c-Jun/AP-1 signaling. Cancer Sci 2004; 95: 176-80.
37. Dent R, Trudeau M, Pritchard K I, et al. Triple-negative breast cancer: clinical features and patterns of recurrence. Clin Cancer Res 2007; 13: 4429-34.
38. Dawson S J, Provenzano E, Caldas C. Triple negative breast cancers: clinical and prognostic implications. Eur J Cancer 2009; 45 Suppl 1: 27-40.
39. Cleator S, Heller W, Coombes R C. Triple-negative breast cancer: therapeutic options. Lancet Oncol 2007; 8: 235-44.
40. Hamilton T C, Young R C, McKoy W M, et al. Characterization of a human ovarian carcinoma cell line (NIH:OVCAR-3) with androgen and estrogen receptors. Cancer Res 1983; 43: 5379-89.
41. Hamilton T C, Young R C, Louie K G, et al. Characterization of a xenograft model of human ovarian carci- 41. noma which produces ascites and intraabdominal carcinomatosis in mice. Cancer Res 1984; 44: 5286-90.
42. Shih le M, Sheu J J, Santillan A, et al. Amplification of a chromatin remodeling gene, Rsf-1/HBXAP, in ovarian carcinoma. Proc Natl Acad Sci U S A 2005; 102: 14004-9.
43. Sheu J J, Choi J H, Yildiz I, et al. The roles of human sucrose nonfermenting protein 2 homologue in the tumor-promoting functions of Rsf-1. Cancer Res 2008; 68: 4050-7.
44. Nalepa G, Rolfe M, Harper J W. Drug discovery in the ubiquitin-proteasome system. Nat Rev Drug Discov 2006; 5: 596-613.
45. Lee B H, Lee M J, Park S, et al. Enhancement of proteasome activity by a small-molecule inhibitor of USP14. Nature 2010; 467: 179-84.
46. Bedford L, Lowe J, Dick L R, Mayer R J, Brownell J E. Ubiquitin-like protein conjugation and the ubiquitin-proteasome system as drug targets. Nat Rev Drug Discov 2011; 10: 29-46.
47. Byrne A, McLaren R P, Mason P, et al. Knockdown of human deubiquitinase PSMD14 induces cell cycle arrest and senescence. Exp Cell Res 2010; 316: 258-71.

What is claimed is:

1. A method of treating cancer, the method comprising administering to the subject a therapeutically effective amount of a polynucleotide agent which hybridizes to a polynucleotide encoding proteasome 26S subunit, non-ATPase PSMD6, and down-regulates expression of said PSMD6, thereby treating the cancer.

2. The method of claim 1, wherein said cancer comprises breast cancer or ovarian cancer.

3. The method of claim 1, wherein said polynucleotide agent comprises an siRNA or shRNA.

4. The method of claim 3, wherein said siRNA comprises the nucleic acid sequence as set forth in SEQ ID NO: 14 or SEQ ID NO: 15.

* * * * *

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: Psmd1 targeting siRNA sense strand sequence

<400> SEQUENCE: 1
ctcatattgg gaatgctta                                                    19

<210> SEQ ID NO 2
<211> LENGTH: 19
<212> TYPE: DNA
<213> ORGANISM: Artificial Sequence
<220> FEATURE:
<223> OTHER INFORMATION: Psmd1 targeting siRNA anti-sense strand
      sequence

<400> SEQUENCE: 2
taagcattcc caatatgag                                                    19

<210> SEQ ID NO 3
<211> LENGTH: 97
<212> TYPE: DNA
<213> ORGANISM: Artificial Sequence
<220> FEATURE:
<223> OTHER INFORMATION: PSDM1-shRNAmir stem and loop sequence

<400> SEQUENCE: 3
tgctgttgac agtgagcgag ctcatattgg gaatgcttat tagtgaagcc acagatgtaa       60
taagcattcc caatatgagc ctgcctactg cctcgga                                97

<210> SEQ ID NO 4
<211> LENGTH: 2990
<212> TYPE: DNA
<213> ORGANISM: Homo sapiens

<400> SEQUENCE: 4
tgcgcgcgca gcgggccggc agtggcggcg gagatggagg agggaggccg ggacaaggcg       60
ccggtgcagc cccagcagtc tccagcggcg gcccccggcg gcacggacga gaagccgagc      120
ggcaaggagc ggcgggatgc cggggacaag gacaaagaac aggagctgtc tgaagaggat      180
aaacagcttc aagatgaact ggagatgctc gtggaacgac taggggagaa ggatacatcc      240
ctgtatcgac cagcgctgga ggaattgcga aggcagattc gttcttctac aacttccatg      300
acttcagtgc ccaagcctct caaatttctg cgtccacact atggcaaact gaaggaaatc      360
tatgagaaca tggcccctgg ggagaataag cgttttgctg ctgacatcat ctccgttttg      420
```

-continued

```
gccatgacca tgagtgggga gcgtgagtgc ctcaagtatc ggctagtggg ctcccaggag    480
gaattggcat catggggtca tgagtatgtc aggcatctgg caggagaagt ggctaaggag    540
tggcaggagc tggatgacgc agagaaggtc cagcgggagc tctgctcac tctggtgaag    600 gaaatcgtcc cctataacat ggcccacaat gcagagcatg aggcttgcga cctgcttatg    660
gaaattgagc aggtggacat gctggagaag gacattgatg aaaatgcata tgcaaaggtc    720
tgcctttatc tcaccagttg tgtgaattac gtgcctgagc ctgagaactc agccctactg    780
cgttgtgccc tgggtgtgtt ccgaaagttt agccgcttcc ctgaagctct gagattggca    840
ttgatgctca atgacatgga gttggtagaa gacatcttca cctcctgcaa ggatgtggta    900
gtacagaaac agatggcatt catgctaggc cggcatgggg tgttcctgga gctgagtgaa    960
gatgtcgagg agtatgagga cctgacagag atcatgtcca atgtacagct caacagcaac   1020
ttcttggcct tagctcggga gctggacatc atggagccca aggtgcctga tgacatctac   1080
aaaacccacc tagagaacaa caggtttggg ggcagtggct ctcaggtgga ctctgcccgc   1140
atgaacctgg cctcctcttt tgtgaatggc tttgtgaatg cagcttttgg ccaagacaag   1200
ctgctaacag atgatggcaa caaatggctt tacaagaaca aggaccacgg aatgttgagt   1260
gcagctgcat ctcttgggat gattctgctg tgggatgtgg atggtggcct cacccagatt   1320
gacaagtacc tgtactcctc tgaggactac attaagtcag gagctcttct gcctgtggc   1380 atagtgaact ctggggtccg gaatgagtgt gaccctgctc tggcactgct tcagactat   1440 gttctccaca acagcaacac catgagactt ggttccatct ttgggctagg cttggcttat   1500
gctggctcaa atcgtgaaga tgtcctaaca ctgctgctgc ctgtgatggg agattcaaag   1560
tccagcatgg aggtggcagg tgtcacagct ttagcctgtg aatgatagc agtagggtcc   1620 tgcaatggag atgtaacttc cactatcctt cagaccatca tggagaagtc agagactgag   1680
ctcaaggata cttatgctcg ttggcttcct cttggactgg gtctcaacca cctggggaag   1740
ggtgaggcca tcgaggcaat cctggctgca ctggaggttg tgtcagagcc attccgcagt   1800
tttgccaaca cactggtgga tgtgtgtgca tatgcaggct ctgggaatgt gctgaaggtg   1860
cagcagctgc tccacatttg tagcgaacac tttgactcca agagaagga ggaagacaaa   1920 gacaagaagg aaaagaaaga caaggacaag aaggaagccc ctgctgacat gggagcacat   1980
cagggagtgg ctgttctggg gattgccctt attgctatgg gggaggagat tggtgcagag   2040
atggcattac gaacctttgg ccacttgctg agatatgggg agcctacact ccggagggct   2100
gtacctttag cactggccct catctctgtt tcaaatccac gactcaacat cctggatacc   2160
ctaagcaaat tctctcatga tgctgatcca gaagtttcct ataactccat tttgccatg    2220 ggcatggtgg gcagtggtac caataatgcc cgtctggctg caatgctgcg ccagttagct   2280
caatatcatg ccaaggaccc aaacaacctc ttcatggtgc gcttggcaca gggcctgaca   2340
catttaggga agggcaccct taccctctgc ccctaccaca cgaccggca gcttatgagc    2400 caggtggccg tggctggact gctcactgtg cttgtctctt tcctggatgt tcgaaacatt   2460
attctaggca aatcacacta tgtattgtat gggctggtgg ctgccatgca gccccgaatg   2520
ctggttacgt ttgatgagga gctgcggcca ttgccagtgt ctgtccgtgt gggccaggca   2580
gtggatgtgg tgggccaggc tggcaagccg aagactatca cagggttcca gacgcataca   2640
accccagtgt tgttggccca cggggaacgg gcagaattgg ccactgagga gtttcttcct   2700
gttaccccca ttctgaaagg ttttgttatc cttcggaaga accccaatta tgatctctaa   2760
gtgaccacca ggggctctga actgcagctg atgttatcag caggccatgc atcctgctgc   2820
```

```
caagggtgga cacggctgca gacttctggg ggaattgtcg cctcctgctc ttttgttact    2880
gagtgagata aggttgttca ataaagactt ttatccccaa ggaaaaaaaa aaaaaaaaaa    2940
aaaaaaaaaa aaaaaaaaaa aaaaaaaaaa aaaaaaaaaa aaaaaaaaaa              2990
```

<210> SEQ ID NO 5
<211> LENGTH: 2174
<212> TYPE: DNA
<213> ORGANISM: Homo sapiens

<400> SEQUENCE: 5

```
agaaggccca gcgccgggaa ggggtttgca gctgctccgt catcgtgcgg cccgacgcta      60
tctcgcgctc gtgtgcaggc ccggctcggc tcctggtccc cggtgcgagg gttaacgcga     120
ggccccggcc tcggtcccg gactaggccg tgaccccggg tgccatgaag caggagggct     180
cggcgcggcg ccgcggcgcg gacaaggcga aaccgccgcc cggcggagga gaacaagaac     240
ccccaccgcc gccggccccc caggatgtgg agatgaaaga ggaggcagcg acgggtggcg     300
ggtcgacggg ggaggcagac ggcaagacgg cggcggcagc ggctgagcac tcccagcgag     360
agctggacac agtcaccttg gaggacatca aggagcacgt gaaacagcta gagaaagcgg     420
tttcaggcaa ggagccgaga ttcgtgctgc gggccctgcg gatgctgcct tccacatcac     480
gccgcctcaa ccactatgtt ctgtataagg ctgtgcaggg cttcttcact tcaaataatg     540
ccactcgaga ctttttgctc cccttcctgg aagagcccat ggacacagag gctgatttac     600
agttccgtcc ccgcacggga aaagctgcgt cgacacccct cctgcctgaa gtggaagcct     660
atctccaact cctcgtggtc atcttcatga tgaacagcaa gcgctacaaa gaggcacaga     720
agatctctga tgatctgatg cagaagatca gtactcagaa ccgccgggcc ctagaccttg     780
tagccgcaaa gtgttactat tatcacgccc gggtctatga gttcctggac aagctggatg     840
tggtgcgcag cttcttgcat gctcggctcc ggacagctac gcttcggcat gacgcagacg     900
ggcaggccac cctgttgaac ctcctgctgc ggaattacct acactacagc ttgtacgacc     960
aggctgagaa gctggtgtcc aagtctgtgt cccagagca ggccaacaac aatgagtggg    1020
ccaggtacct ctactacaca gggcgaatca agccatcca gctggagtac tcagaggccc    1080
ggagaacgat gaccaacgcc cttcgcaagg cccctcagca cacagctgtc ggcttcaaac    1140
agacggtgca caagcttctc atcgtggtgg agctgttgct gggggagatc cctgaccggc    1200
tgcagttccg ccagccctcc ctcaagcgct cactcatgcc ctatttcctt ctgactcaag    1260
ctgtcaggac aggaaaccta gccaagttca ccaggtcct ggatcagttt ggggagaagt    1320
ttcaagcaga tgggacctac accctaatta tccggctgcg gcacaacgtg attaagacag    1380
gtgtacgcat gatcagcctc tcctattccc gaatctcctt ggctgacatc gcccagaagc    1440
tgcagttgga tagccccgaa gatgcagagt tcattgttgc caaggccatc cgggatggtg    1500
tcattgaggc cagcatcaac cacgagaagg ctatgtcca atccaaggag atgattgaca    1560
tctattccac ccgagagccc cagctagcct tccaccagcg catctccttc tgcctagata    1620
tccacaacat gtctgtcaag gccatgaggt ttcctcccaa atcgtacaac aaggacttgg    1680
agtctgcaga ggaacggcgt gagcgagaac agcaggactt ggagtttgcc aaggagatgg    1740
cagaagatga tgatgacagc ttcccttgag ctggggggct gggagggggt aggggaatg    1800 gggacaggct ctttcccct tggggtccc ctgcccaggg cactgtcccc attttcccac    1860
acacagctca tatgctgcat tcgtgcaggg ggtgggggtg ctgggagcca gccaccctga    1920
```

```
cctcccccag ggctcctccc cagccggtga cttactgtac agcaggcagg agggtgggca      1980
ggcaacctcc ccgggcaggg tcctggccag cagtgtggga gcaggagggg aaggatagtt      2040
ctgtgtactc ctttagggag tgggggacta gaactgggat gtcttggctt gtatgttttt      2100
tgaagcttcg attatgattt ttaaacaata aaaagttctc cacagtgaaa aaaaaaaaa       2160 aaaaaaaaaa aaaa                                                         2174
```

<210> SEQ ID NO 6
<211> LENGTH: 1332
<212> TYPE: DNA
<213> ORGANISM: Homo sapiens

<400> SEQUENCE: 6

```
aattggagga gttgttgtta ggccgtcccg agacccggt cgggagggag gaaggtggca        60
agatggtgtt ggaaagcact atggtgtgtg tggacaacag tgagtatatg cggaatggag      120
acttcttacc caccaggctg caggcccagc aggatgctgt caacatagtt tgtcattcaa      180
agacccgcag caaccctgag aacaacgtgg gccttatcac actggctaat gactgtgaag      240
tgctgaccac actcacccca gacactggcc gtatcctgtc caagctacat actgtccaac      300
ccaagggcaa gatcaccttc tgcacgggca tccgcgtggc ccatctggct ctgaagcacc      360
gacaaggcaa gaatcacaag atgcgcatca ttgcctttgt gggaagccca gtggaggaca      420
atgagaagga tctggtgaaa ctggctaaac gcctcaagaa ggaaaagta aatgttgaca       480 ttatcaattt tggggaagag gaggtgaaca cagaaaagct gacagccttt gtaaacacgt      540
tgaatggcaa agatggaacc ggttctcatc tggtgacagt gcctcctggg cccagtttgg      600
ctgatgctct catcagttct ccgattttgg ctggtgaagg tggtgccatg ctgggtcttg      660
gtgccagtga ctttgaattt ggagtagatc ccagtgctga tcctgagctg gccttggccc      720
ttcgtgtatc tatggaagag cagcggcagc ggcaggagga ggaggcccgg cgggcagctg      780
cagcttctgc tgctgaggcc gggattgcta cgactgggac tgaagactca gacgatgccc      840
tgctgaagat gaccatcagc cagcaagagt ttggccgcac tgggcttcct gacctaagca      900
gtatgactga ggaagagcag attgcttatg ccatgcagat gtccctgcag ggagcagagt      960
ttggccaggc ggaatcagca gacattgatg ccagctcagc tatggacaca tctgagccag     1020
ccaaggagga ggatgattac gacgtgatgc aggaccccga gttccttcag agtgtcctag     1080
agaacctccc aggtgtggat cccaacaatg aagccattcg aaatgctatg ggctccctgg     1140
cctcccaggc caccaaggac ggcaagaagg acaagaagga ggaagacaag aagtgagact     1200
ggagggaaag ggtagctgag tctgcttagg ggactgcatg ggaagcacgg aatataggt     1260 tagatgtgtg ttatctgtaa ccattacagc ctaaataaag cttggcaact tttttttcctt    1320 ttttgcttca aa                                                        1332
```

<210> SEQ ID NO 7
<211> LENGTH: 1308
<212> TYPE: DNA
<213> ORGANISM: Homo sapiens

<400> SEQUENCE: 7

```
gtcagccgct gtcccttag ccgcgatgcc gctggagaac ctggaggagg agggtctgcc        60
caagaacccc gacttgcgta tcgcgcagct gcgcttcctg ctcagcctgc ccagcaccg       120 cggagacgct gccgtgcgcg acgagctgat ggcggccgtc cgcgataaca acatggctcc     180
ttactatgaa gccttgtgca aatccctcga ctggcagata gacgtggacc tactcaataa     240
```

```
aatgaagaag gcaaatgaag atgagttgaa gcgtttggat gaggagctgg aagatgcaga      300
gaagaatcta ggagagagcg aaattcgcga tgcaatgatg gcaaaggccg agtacctctg      360
ccggataggt gacaaagagg gagctctgac agcctttcgc aagacatatg acaaaactgt      420
ggccctgggt caccgattgg atattgtatt ctatctcctt aggattggct tattttatat      480
ggataatgat ctcatcacac gaaacacaga aaaggccaaa agcttaatag aagaaggagg      540
agactgggac aggagaaacc gcctaaaagt gtatcagggt ctttattgtg tggctattcg      600
tgatttcaaa caggcagctg aactcttcct tgacactgtt tcaacattta catcctatga      660
actcatggat tataaaacat tgtgacttta tactgtctat gtcagtatga ttgccttaga      720
aagaccagat ctcagggaaa aggtcattaa aggagcagag attcttgaag tgttgcacag      780
tcttccagca gttcggcagt atctgttttc actctatgaa tgccgttact ctgtttttctt      840 ccaatcatta gcggttgtgg aacaggaaat gaaaaaggac tggcttttg ccctcatta       900 tcgatactat gtaagagaaa tgagaattca tgcatacagt cagctgctgg aatcatatag      960
gtcattaacc cttggctata tggcagaagc gtttggtgtt ggtgtggaat tcattgatca     1020
ggaactgtcc aggtttattg ctgccgggag actacactgc aaaatagata agtgaatga     1080 aatagtagaa accaacagac ctgatagcaa gaactggcag taccaagaaa ctatcaagaa     1140
aggagatctg ctactaaaca gagttcaaaa acttccaga gtaattaata tgtaaagcca      1200
tgtaactaac aaaggatttg ctttagagat aattatttgg aatttttata gcttacttca     1260
caatgtgccc aggtcagctg tataaaataa atactgcatt gttgtttc                 1308

<210> SEQ ID NO 8
<211> LENGTH: 1686
<212> TYPE: DNA
<213> ORGANISM: Homo sapiens

<400> SEQUENCE: 8
gggagcggaa gaaggaggcc gcgcgagggc tgacgaaccg gaagaagagg aactgggcct       60
gaaagggtac cggtgaccgc tactgctgcc ggtgtttgcg tgtggcaggg agccaggcct      120
ggcgagcggg gtgtgtcgcg atgccggagc tggcagtgca gaaggtggtg gtccaccccc      180
tggtgctgct cagtgtggtg gatcatttca accgaatcgg caaggttgga aaccagaagc      240
gtgttgttgg tgtgcttttg gggtcatggc aaaagaaagt acttgatgta tcgaacagtt      300
ttgcagttcc ttttgatgaa gatgacaaag acgattctgt atggtttta gaccatgatt      360 atttggaaaa catgtatgga atgtttaaga agtcaatgc cagggaaaga atagttggct      420
ggtaccacac aggccctaaa ctacacaaga atgacattgc catcaacgaa ctcatgaaaa      480
gatactgtcc taattccgta ttggtcatca ttgatgtgaa gccgaggac ctagggctgc       540 ctacagaagc gtacatttca gtggaagaag tccatgatga tggaactcca acctcgaaaa      600
catttgaaca cgtgaccagt gaaattggag cagaggaagc tgaggaagtt ggagttgaac      660
acttgttacg agatatcaaa gacacgacgg tgggcactct gtcccagcgg atcacaaacc      720
aggtccatgg tttgaaggga ctgaactcca agcttctgga tatcaggagc tacctggaaa      780
aagtcgccac aggcaagctg cccatcaacc accagatcat ctaccagctg caggacgtct      840
tcaacctgct gccagatgtc agcctgcagg agttcgtcaa ggcctttttac ctgaagacca      900 atgaccagat ggtggtagtg tacttggcct cgctgatccg ttccgtggtc gccctgcaca      960
acctcatcaa caacaagatt gccaaccggg atgcagagaa gaaagaaggg caggagaaag     1020
```

| | |
|---|---|
| aagagagcaa aaaggatagg aaagaggaca aggagaaaga taaagataag gaaaagagtg | 1080 |
| atgtaaagaa agaggagaaa aaggagaaaa agtaaaacat gtattaaata gcttttttaa | 1140 |
| tttgtaaatt aaaatcttac aaactaaatc agtgtgctgc tagagggttc ttttttcactt | 1200 |
| gacatgctta ttagaaagct gacccaacaa gagctctctg cctccggtca ctcttgctgt | 1260 |
| ggtgctacgt ggaagtgaat ggagactgat ctcaaatctg aactgcagct ttcgctgctg | 1320 |
| tgagttgggg atatgatagt cagctcaggc ttcagattgt atgagaaaaa tgaagagaag | 1380 |
| tcaacaaata ttttggtact cttcattcat ttatctctaa aaccaggagt tgaattttcc | 1440 |
| tcatcttgaa agactcttgg ggtctgtttc tggtatttta caaaattgct aagtggaatg | 1500 |
| catgaattgc attatgttct ctggtaacac gtagagttca gacccttctg aactctgttg | 1560 |
| ataataccac accatgttct ggacccatag ctctggcatc ctcaggggtt gtgatccagc | 1620 |
| tccatatatt gtttaccttc aaagatacaa ttaaatggct tgattttttaa aaaaaaaaaa | 1680 |
| aaaaaa | 1686 |

<210> SEQ ID NO 9
<211> LENGTH: 1556
<212> TYPE: DNA
<213> ORGANISM: Homo sapiens

<400> SEQUENCE: 9

| | |
|---|---|
| ccaacttccg gtcaccatct tgagtgacga cagaggcgga gctccaactg acatgttcat | 60 |
| taagggcagg gctccgaggg cgccacctcg agagcgacgg cgggctaccc ggggcgggct | 120 |
| gaggcaggtt gtagccccgc cccgggcctt gggctccacc tctcggcccc acttccgccg | 180 |
| ggcaagcgtt tgtaggcggc gctgccgtaa atcaggcggt ctgcttgccg catcacgcaa | 240 |
| gatggcggcc gcgcggtga acggggcggc aggcttctcg agctccgggc ccgcggcaac | 300 |
| ctcgggcgct gttctgcagg ccgcgaccgg catgtacgag caactcaagg gcgagtggaa | 360 |
| ccgtaaaagc cccaatctta gcaagtgcgg ggaagagctg ggtcgactca agctagttct | 420 |
| tctggagctc aacttcttgc caaccacagg gaccaagctg accaaacagc agctaattct | 480 |
| ggcccgtgac atactggaga tcggggccca atggagcatc ctacgcaagg acatcccctc | 540 |
| cttcgagcgc tacatggccc agctcaaatg ctactacttt gattacaagg agcagctccc | 600 |
| cgagtcagcc tatatgcacc agctcttggg cctcaacctc ctcttcctgc tgtcccagaa | 660 |
| ccgggtggct gagttccaca cggagttgga gcggctgcct gccaaggaca tacagaccaa | 720 |
| tgtctacatc aagcacccag tgtccctgga gcaatacctg atggagggca gctacaacaa | 780 |
| agtgttcctg gccaagggta acatccccgc cgagagctac accttcttca ttgacatcct | 840 |
| gctcgacact atcagggatg agatcgctgg gtgcatcgag aaggcctacg agaaaatcct | 900 |
| tttcactgag gccacccgga tcctcttctt caacacaccc aaaaagatga cagactacgc | 960 |
| caagaagcga gggtgggtcc tgggccccaa caactactac agttttgcca gccagcagca | 1020 |
| gaagccggaa gacaccacca ttccctccac agaactggcc aaacaggtca tcgagtatgc | 1080 |
| ccggcagctg gagatgatcg tctgagcccc ccgggcactg ggtggggcag ggcacgagtt | 1140 |
| atttaaaaca gttacactgc agggtttcgc ccaataaagg tggactgaca ttccctcttc | 1200 |
| caggcccttg tctccccagt tgggacggca gagagacaag ttcttatatc tgaagaactt | 1260 |
| ggaggttttg gggcattcag gagttggaga tagcctccaa ctgggtcagc ctctgtctgg | 1320 |
| tgggcattgc tcagggtctc aaacatggac gcccactgtg gggccccagc agcactgtgg | 1380 |
| cctgcaggag ggcatggccc caggtagggg gactgttcta gccagctgtg gacacatagg | 1440 |

| aatgctggac cagggtacca gattttttca acaaagggggg tgaagtgtcc tactaaaaag | 1500 |
| aataaatgtt ggcagtgaat taaacaattt ttcaaatgaa aaaaaaaaaa aaaaaa | 1556 |

<210> SEQ ID NO 10
<211> LENGTH: 1814
<212> TYPE: DNA
<213> ORGANISM: Homo sapiens

<400> SEQUENCE: 10

| ctgagcgggt gcgcgggcaa cttccggtgt gggtgacgag tggtggccga agcaggggga | 60 |
| cagcaaggga cgctcaggcg gggaccatgg cggacggcgg ctcggagcgg gctgacgggc | 120 |
| gcatcgtcaa gatggaggtg gactacagcg ccacggtgga tcagcgccta cccgagtgtg | 180 |
| cgaagctagc caaggaagga agacttcaag aagtcattga aacccttctc tctctggaaa | 240 |
| agcagactcg tactgcttcc gatatggtat cgacatcccg tatcttagtt gcagtagtga | 300 |
| agatgtgcta tgaggctaaa gaatgggatt tacttaatga aaatattatg cttttgtcca | 360 |
| aaaggcggag tcagttaaaa caagctgttg ccaaaatggt tcaacagtgc tgtacttatg | 420 |
| ttgaggaaat cacagacctt cctatcaaac ttcgattaat tgatactcta cgaatggtta | 480 |
| ccgaaggcaa gatttatgtt gaaattgagc gtgcgcgact gactaaaaca ttagcaacta | 540 |
| taaaagaaca aaatggtgat gtgaagagg cagcctccat tttacaggag ttacaggtgg | 600 |
| aaacctacgg gtcaatggaa aagaaagagc gagtggaatt tattttggag caaatgaggc | 660 |
| tctgcctagc tgtgaaggat tacattcgaa cacaaatcat cagcaagaaa attaacacca | 720 |
| aattttttcca ggaagaaaat acagagaaat taaagttgaa gtactataat ttaatgattc | 780 |
| agctggatca acatgaggga tcctatttgt ctatttgtaa gcactacaga gcaatatatg | 840 |
| atactccctg tatacaggca gaaagtgaaa atggcagca ggctctgaag agtgttgtac | 900 |
| tctatgttat cctggctcct tttgacaatg aacagtcaga tttggttcac cgaataagtg | 960 |
| gtgacaagaa gttagaagaa attcccaaat acaaggatct tttaaagctt tttaccacaa | 1020 |
| tggagttgat gcgttggtcc acacttgttg aggactatgg aatggaatta agaaaaggtt | 1080 |
| cccttgagag tcctgcaacg gatgttttg gttctacaga ggaaggtgaa aaaaggtgga | 1140 |
| aagacttgaa gaacagagtt gttgaacata atattagaat aatggccaag tattatactc | 1200 |
| ggataacaat gaaaaggatg gcacagcttc tggatctatc tgttgatgag tccgaagcct | 1260 |
| ttctctcaaa tctagtagtt aacaagacca tctttgctaa agtagacaga ttagcaggaa | 1320 |
| ttatcaactt ccagagaccc aaggatccaa ataatttatt aaatgactgg tctcagaaac | 1380 |
| tgaactcatt aatgtctctg gttaacaaaa ctacgcatct catagccaaa gaggagatga | 1440 |
| tacataatct acaataaggg tcttagtgct ttagaaaaaa gttaaaattg gaagtcatta | 1500 |
| aaaaaagact gttataatgg tgtatatgtt ggggtttttt ttctaagctt ctttgtctta | 1560 |
| aattttaaaa tagtgaatat gtttgagact ccctttgacc tttcagttcc ccaagttcat | 1620 |
| tgttaacttt gcatttgcaa ttggtgcaaa aatacagatt tctgtcgtct gaatacacaa | 1680 |
| aaagttgtgt cataacttac ccagatatgt ttttctatca tttgaaacct ttttagctac | 1740 |
| tgtttgtttt cattcaacta acaaacatat tccaataata aaagcagtat atacataaaa | 1800 |
| aaaaaaaaaa aaaa | 1814 |

<210> SEQ ID NO 11
<211> LENGTH: 3236
<212> TYPE: DNA

<213> ORGANISM: Homo sapiens

<400> SEQUENCE: 11

```
ggggtcctgg cgagaagcga gccggcggcc tgaggaggcg actgactgag cagcgcaccc      60
ggggagcaag gaggcgcggt gaactgagcg gcccctgagc tgacagatac actgcgcagc     120
tggaacggcg agcgagccga cgggcgagtg aggggcgcag ccatgatcac ctcggccgct     180
ggaattattt ctcttctgga tgaagatgaa ccacagctta aggaatttgc actacacaaa     240
ttgaatgcag ttgttaatga cttctgggca gaaatttccg agtccgtaga caaaatagag     300
gttttatacg aagatgaagg tttccggagt cggcagtttg cagccttagt ggcatctaaa     360
gtattttatc acctgggggc ttttgaggag tctctgaatt atgctcttgg agcaggggac     420
ctcttcaatg tcaatgataa ctctgaatat gtggaaacta ttatagcaaa atgcattgat     480
cactacacca aacaatgtgt ggaaaatgca gatttgcctg aaggagaaaa aaaaccaatt     540
gaccagagat tggaaggcat cgtaaataaa atgttccagc gatgtctaga tgatcacaag     600
tataaacagg ctattggcat tgctctggag acacgaagac tggacgtctt tgaaaagacc     660
atactggagt cgaatgatgt cccaggaatg ttagcttata gccttaagct ctgcatgtct     720
ttaatgcaga ataaacagtt tcggaataaa gtactaagag ttctagttaa aatctacatg     780
aacttggaga aacctgattt catcaatgtt tgtcagtgct taattttctt agatgatcct     840
caggctgtga gtgatatctt agagaaactg gtaaaggaag acaacctcct gatggcatat     900
cagatttgtt ttgatttgta tgaaagtgct agccagcagt ttttgtcatc tgtaatccag     960
aatcttcgaa ctgttggcac ccctattgct tctgtgcctg gatccactaa tacgggtact    1020
gttccgggat cagagaaaga cagtgactcg atggaaacag aagaaaagac aagcagtgca    1080
tttgtaggaa agacaccaga agccagtcca gagcctaagg accagacttt gaaaatgatt    1140
aaaattttaa gtggtgaaat ggctattgag ttacatctgc agttcttaat acgaaacaat    1200
aatacagacc tcatgattct aaaaaacaca aaggatgcag tacggaattc tgtatgtcat    1260
actgcaaccg ttatagcaaa ctcttttatg cactgtggga caaccagtga ccagtttctt    1320
agagataatt tggaatggtt agccagagcc actaactggg caaaatttac tgctacagcc    1380
agtttgggtg taattcataa gggtcatgaa aaagaagcat acagttaat ggcaacatac    1440
cttcccaagg atacttctcc aggatcagcc tatcaggaag gtggaggtct ctatgcacta    1500
ggtcttattc atgccaatca tggtggtgat ataattgact atctgcttaa tcagcttaag    1560
aacgccagca tgatatcgt tagacacggt ggcagtctgg gccttggttt ggcagccatg    1620
ggaactgcac gtcaagatgt ttatgatttg ctaaaaacaa acctttatca ggatgatgca    1680
gtaacagggg aagcagctgg cctggcccta ggtttggtta tgttgggctc taaaaatgct    1740
caggctattg aggacatggt tggttatgca caagaaactc aacatgagaa gattctgcgt    1800
ggtcttgcag ttggcatagc tttagtaatg tatgggagga tggaagaggc tgatgctctc    1860
attgaatctc tctgtcgtga caaggaccca attcttcgaa ggtctggaat gtatactgta    1920
gccatggctt attgtggctc tggtaacaac aaagcaattc gacgcctgct acatgttgct    1980
gtaagtgatg ttaatgatga tgtcaggagg gcagcagtag aatcacttgg gttcattcta    2040
ttcagaaccc ctgaacagtg cccaagtgtt gtctctttgt tgtcagagag ttacaaccct    2100
catgtgcgct acggagctgc aatggccttg gggatatgct gtgctggtac aggaaacaag    2160
gaagccatta atttgctaga accaatgaca acgaccccg tgaactacgt gaggcaaggg    2220
gcactcatag cttcagctct catcatgatc cagcagactg aaatcacttg tccaaaggtg    2280
```

```
aatcagttca gacagctgta ttccaaagtc atcaatgata agcatgatga tgtcatggcc      2340
aagtttggcg ctattctggc ccagggcata ctggatgcag gtggtcataa tgtcacaatc      2400
tccttgcagt ccaggactgg gcatactcat atgccttctg tggttggcgt ccttgtattt      2460
acccagtttt ggttctggtt tcctctttca cacttcctgt cattggctta taccccgtacc     2520 tgtgtcattg gccttaacaa ggacttaaag gtttctactg ctgtattatc tataactgcc      2580
aaggctaaaa agaaggaaaa agaaaaggaa aaaaggagg aggagaaaat ggaagtggat       2640
gaggcagaga aaaggagga aaagagaag aaaaagaac ctgagccaaa cttccagtta         2700
ttggataacc cagcccgagt tatgcctgcc cagcttaagg tcctaaccat gccggagacc      2760
tgtagatacc agcctttcaa accactctct attggaggca tcatcattct gaaggatacc      2820
agtgaagaca ttgaggagct ggtggaacct gtggcagcac atggcccaaa atcgaggag       2880 gaggaacaag agccagaacc cccagaacca tttgagtata ttgatgatta agggccagag      2940
gatctcactt gcttatctga agaagattgt ccaggctcat attgggaatg cttatgagga     3000
aattcatgcc gagacctgct attcaatgca tgtatcgttg cctctgcact gacctgaaga     3060
accctgtctc caagtctttg gttgaagaga agatatatga ctgttgagtg tgctctttca     3120
cagaacttgg ttttcaaata aatataagat ctccagatgg acaagacatt tgttttttcag    3180 cctgggtttt taataaatgt atctaatcct ccccacacca tgaaatgcct aaaaaa         3236

<210> SEQ ID NO 12
<211> LENGTH: 3329
<212> TYPE: DNA
<213> ORGANISM: Homo sapiens

<400> SEQUENCE: 12
ggggtcctgg cgagaagcga gccggcggcc tgaggaggcg actgactgag cagcgcaccc        60
ggggagcaag gaggcgcggt gaactgagcg gcccctgagc tgacagatac actgcgcagc      120
tggaacggcg agcgagccga cgggcgagtg aggggcgcag ccatgatcac ctcggccgct      180
ggaattattt ctcttctgga tgaagatgaa ccacagctta aggaatttgc actacacaaa      240
ttgaatgcag ttgttaatga cttctgggca gaaatttccg agtccgtaga caaaatagag      300
gttttatacg aagatgaagg tttccggagt cggcagtttg cagccttagt ggcatctaaa      360
gtattttatc acctggggc ttttgaggag tctctgaatt atgctcttgg agcagggac        420 ctcttcaatg tcaatgataa ctctgaatat gtggaaacta ttatagcaaa atgcattgat      480
cactacacca aacaatgtgt ggaaaatgca gatttgcctg aaggagaaaa aaaccaatt      540 gaccagagat tggaaggcat cgtaaataaa atgttccagc gatgtctaga tgatcacaag      600
tataaacagg ctattggcat tgctctggag acacgaagac tggacgtctt tgaaaagacc      660
atactggagt cgaatgatgt cccaggaatg ttagcttata gccttaagct ctgcatgtct      720
ttaatgcaga ataaacagtt tcggaataaa gtactaagag ttctagttaa aatctacatg      780
aacttggaga aacctgattt catcaatgtt tgtcagtgct taattttctt agatgatcct      840
caggctgtga gtgatatctt agagaaactg gtaaaggaag acaacctcct gatggcatat      900
cagatttgtt ttgatttgta tgaaagtgct agccagcagt ttttgtcatc tgtaatccag      960
aatcttcgaa ctgttggcac ccctattgct tctgtgcctg atccactaa tacgggtact      1020 gttccgggat cagagaaaga cagtgactcg atggaaacag aagaaagac aagcagtgca      1080 tttgtaggaa agacaccaga agccagtcca gagcctaagg accagacttt gaaaatgatt     1140
```

```
aaaattttaa gtggtgaaat ggctattgag ttacatctgc agttcttaat acgaaacaat    1200
aatacagacc tcatgattct aaaaaacaca aaggatgcag tacggaattc tgtatgtcat    1260
actgcaaccg ttatagcaaa ctcttttatg cactgtggga caaccagtga ccagtttctt    1320
agagataatt tggaatggtt agccagagcc actaactggg caaaatttac tgctacagcc    1380
agtttgggtg taattcataa gggtcatgaa aaagaagcat acagttaatg gcaacatac     1440 cttcccaagg atacttctcc aggatcagcc tatcaggaag gtggaggtct ctatgcacta    1500
ggtcttattc atgccaatca tggtggtgat ataattgact atctgcttaa tcagcttaag    1560
aacgccagca atgatatcgt tagacacggt ggcagtctgg ccttggtttt ggcagccatg    1620
ggaactgcac gtcaagatgt ttatgatttg ctaaaaacaa acctttatca ggatgatgca    1680
gtaacagggg aagcagctgg cctggcccta ggtttggtta tgttgggctc taaaaatgct    1740
caggctattg aggacatggt tggttatgca caagaaactc aacatgagaa gattctgcgt    1800
ggtcttgcag ttggcatagc tttagtaatg tatgggagga tggaagaggc tgatgctctc    1860
attgaatctc tctgtcgtga caaggaccca attcttcgaa ggtctggaat gtatactgta    1920
gccatggctt attgtggctc tggtaacaac aaagcaattc gacgcctgct acatgttgct    1980
gtaagtgatg ttaatgatga tgtcaggagg gcagcagtag aatcacttgg gttcattcta    2040
ttcagaaccc ctgaacagtg cccaagtgtt gtctctttgt tgtcagagag ttacaaccct    2100
catgtgcgct acgagctgc aatggccttg gggatatgct gtgctggtac aggaaacaag    2160
gaagccatta atttgctaga accaatgaca aacgaccccg tgaactacgt gaggcaaggg    2220
gcactcatag cttcagctct catcatgatc cagcagactg aaatcacttg tccaaaggtg    2280
aatcagttca gacagctgta ttccaaagtc atcaatgata agcatgatga tgtcatggcc    2340
aagtttggcg ctattctggc ccagggcata ctggatgcag gtggtcataa tgtcacaatc    2400
tccttgcagt ccaggactgg gcatactcat atgccttctg tggttggcgt ccttgtattt    2460
acccagtttt ggttctggtt tcctctttca cacttcctgt cattggctta tacccctacc    2520
tgtgtcattg gccttaacaa ggacttaaag atgccgaaag ttcagtataa atcgaactgt    2580
aaaccatcca catttgcata tcctgcccct ctggaagtac caaagagaaaa agaaaaggaa    2640 aaggtttcta ctgctgtatt atctataact gccaaggcta aaaagaagga aaaagaaaag    2700
gaaaaaaagg aggaggagaa aatggaagtg gatgaggcag agaaaaagga ggaaaaagag    2760
aagaaaaaag aacctgagcc aaacttccag ttattggata cccagcccg agttatgcct    2820 gcccagctta aggtcctaac catgccggag acctgtagat accagccttt caaaccactc    2880
tctattggag gcatcatcat tctgaaggat accagtgaag acattgagga gctggtggaa    2940
cctgtggcag cacatggccc aaaaatcgag gaggaggaac aagagccaga acccccagaa    3000
ccatttgagt atattgatga ttaagggcca gaggatctca cttgcttatc tgaagaagat    3060
tgtccaggct catattggga atgcttatga ggaaattcat gccgagacct gctattcaat    3120
gcatgtatcg ttgcctctgc actgacctga agaaccctgt ctccaagtct ttggttgaag    3180
agaagatata tgactgttga gtgtgctctt tcacagaact tggttttcaa ataaatataa    3240
gatctccaga tggacaagac atttgttttt cagcctgggt ttttaataaa tgtatctaat    3300 cctcccaca ccatgaaatg cctaaaaaa                                        3329
```

<210> SEQ ID NO 13
<211> LENGTH: 3914
<212> TYPE: DNA
<213> ORGANISM: Homo sapiens

<400> SEQUENCE: 13

```
tttccgggtg tgtgtttccg gcgtcggcgg ccgcggccgg ggacggtgtg agagcggtaa      60
gatggcggcg gcggcggtgg tggagttcca gagagcccag tctctactca gcaccgaccg     120
ggaggcctcc atcgacatcc tccactccat cgtgaagcgt gacattcagg aaaacgatga     180
agaggcagtg caagtcaaag agcagagcat cctggaactg ggatctctcc tggcaaagac     240
tggacaagct gcagagcttg gaggactcct gaagtatgta cgaccttct tgaattccat      300
cagcaaggct aaagcagctc gcctggtccg atctcttctt gatctgtttc ttgatatgga     360
agcagctaca gggcaggagg tcgagctgtg tttagagtgc atcgaatggg ccaagtcaga     420
gaaaagaact ttcttacgcc aagctttgga ggcaagactg gtgtctttgt actttgatac     480
caagaggtac caggaagcat tgcatttggg ttctcagctg ctgcgggagt tgaaaaagat     540
ggacgacaaa gctctttttgg tggaagtaca gcttttagaa agcaaaacat accatgccct    600
gagcaacctg ccgaaagccc gagctgcctt aacttctgct cgaaccacag caaatgccat     660
ctactgcccc cctaaattgc aggccacctt ggacatgcag tcgggtatta ccatgcagc      720
agaagagaag gactggaaaa ctgcgtactc atacttctat gaggcatttg agggttatga     780
ctccatcgac agccccaagg ccatcacatc tctgaagtac atgttgctgt gcaaaatcat     840
gctcaacacc ccagaagatg tccaggcttt ggtgagcggg aagcttgcac ttcggtatgc     900
agggaggcag acagaagcat aaaatgcgt ggctcaggct agcaagaaca gatcactggc      960
agattttgaa aaggctctga cagattaccg ggcagagctc cgggatgacc caatcatcag    1020
cacacacttg gccaagttgt atgataactt actagaacag aatctgatcc gagtcattga    1080
gccttttttcc agagtacaga ttgaaacacat atctagtctc atcaaactct ccaaggccga   1140
cgtggaaagg aaattatcac agatgattct tgacaagaaa tttcatggga ttttggacca    1200
gggggagggt gtcctgatta ttttcgatga accccagta gataaaactt acgaagctgc     1260
tctggaaaca attcagaaca tgagcaaagt agtggattcc ctctacaaca aagccaagaa    1320
actgacatag agttggatct gtagcggtcc tttggagagt gtgtgtggcg ggagagtgaa    1380
accttggggg aaaatgctag agattctttt ttctttttg ttctactttt cgctcggaaa     1440
gtttttaaat cctcatttgg tgcatctgta ttccagccaa taggtgtgcc agttttcatg    1500
taatctttac tgggccaact tgggagtggg gaaattgctt aaaaaaaag aaaagaaaa      1560
aaaaaagat tattctaaat aaaaggaaaa aggcttacac tacctaaagc tgtgctctct     1620
gcctcctggg agagggccgc aaagccaggc accccgccaa ccactggggg tcctaatcca    1680
cctgctgggc atcacctctc ctcctcctca gaattgggtg tttgctgacc atcaaaagca    1740
atgactttt attctgtttg tactgaacca aaacaaacaa ctgtgtatag actgctgttt    1800
tcttttttat ttgaaatgag gcattttggt gttctttccc ctaccatacg gcctgtctgc    1860
ccttccctcc ccacattggc tccagcagag tagccgaagg tcctgccgcc gccgccacca    1920
ccaccaccac tgcagcaaca acagcagcag cagcagcagc gcctgcatag ctccactctg    1980
acctgtgaag gaatggggat gaggccagga gctagtgtct accacggcca cacagggagc    2040
agtgtgggcc cttagccccc aagggggcctg ctatgcatgt ggctttttttt ttttttttaa   2100
acacagtaaa ctagattagt cgtcagtgtt ttaattgccc ctcttctcct ctcctgcatt    2160
cctctcctct cttctttcct ctctgtccct tctctttccc ctctcaacca ggagaccatc    2220
atgtctctct gccttcctcc tctcccctcc aggggagtca ggctgtctgt gaaagccatg    2280
```

```
agcttctctc cctctcccac tcctcctctc ctactttcag atggatttat tcctttttta    2340
aacaatgaac atcggaaatg agactgtggg gtgtggtttc tctctctctt ttttttttaa    2400
ttttctttgt tgggtttttg agcaacctca tgtccccttc ccagggagct ttttaattta    2460
cctcttagaa ctcaagtgga tgggaagtag agcactatgt gtcagtatgc tttgttttct    2520
gacacgatta cacagcgagg ctttaatgcc atttgggtag gtgagcttct gcacttctgt    2580
tgtgctgaac tgtattttct tctctcatct cctctttgtc tttttctctt ttcctctcct    2640
tcctgccttc ttctgctggc ctcctttttct cttttcttttac cttccttgga ttatccttcc    2700
aggttttcat aataaattta tattttgtaa aaggattttg ttgtaccagg ttttgcatcc    2760
tcactgaatc tgactggctt ttattttcct ctccaaaatc aggtttttgt tctcaacatc    2820
tttccccatc atgtctagtc actgttttgg ttttggcacc atcagtatca aatgtacaaa    2880
cggttcttgc taaccaacac caggtatatc tgatgttcag atgagttcca ataaaaataa    2940
tttttttttt tttcaaaagg tgtctttttc ttgagtgctg gagggcttcc aagcaagtcc    3000
agacagctct gtgtggcccc cactagtct agctctcatc tggccaaagc tgttatctca    3060
tttgtgtaat gggagtcctt aaggtaaatt tggggtccaa acttggaggg ctttgggggc    3120
aagaaagttg gtgtgtgagt tctgaggttg gaaatgagtt caggtgtctt cttccagggc    3180
agcatggtcc agtgagcaca tgtaagtttg ggcagtagat cctctgagcc tactttctct    3240
tctactcagt gaggatgctg cttccttggc aggtgattgt gatgtgaagc ttagtaagtc    3300
atagacgtgc aggtgtctgg agagtcctga catgcagttg tggtttcgtt tccttttgga    3360
atcttcaaag gcagcgattt tcatattgcc tcacaccctg gcgggggcgg ggggctctgg    3420
gaccactggg ggacctgcta aatcctcttc agtctgagca gttcagccat tgtcagtttt    3480
agtattgtgt ctctgtattt cacttgcaga aagagctttg cttctataaa ggactttaaa    3540
aagtactcca aagagatcta gttttggagt agaggggaga tgttttctca aacttagggc    3600
agtcctgaga tgctcaggca gtagcccttt tctcagttcc ctttgcgggt cttggtcaga    3660
tgatgccctc tagacccgtg ctgtccaata tgtagccgct agccatgtgc agctgtcagg    3720
cccttgcaac gtggctggtt cgagctgtga tacactgcaa gtgtaaacac aaaccagact    3780
tcgaaggctt agtatgataa caaaagaaaa ggagtgtaaa atatgtcaat aactttttta    3840
tatatgtgtt gaaatatttt gggtattggg ttaaataaaa tatattatta aaattcaaaa    3900
aaaaaaaaaa aaaa                                                     3914

<210> SEQ ID NO 14
<211> LENGTH: 21
<212> TYPE: DNA
<213> ORGANISM: Artificial sequence
<220> FEATURE:
<223> OTHER INFORMATION: Psmd6 targeting shRNA anti-sense strand
      sequence

<400> SEQUENCE: 14
aataaacctg gacagttcct g                                              21

<210> SEQ ID NO 15
<211> LENGTH: 21
<212> TYPE: DNA
<213> ORGANISM: Artificial sequence
<220> FEATURE:
<223> OTHER INFORMATION: Psmd6 targeting shRNA anti-sense strand
      sequence

<400> SEQUENCE: 15
```
aatgacctat atgattccag c                                              21

<210> SEQ ID NO 16
<211> LENGTH: 21
<212> TYPE: DNA
<213> ORGANISM: Artificial sequence
<220> FEATURE:
<223> OTHER INFORMATION: Psmd11 targeting shRNA anti-sense strand
      sequence

<400> SEQUENCE: 16
ataatacccg actgcatgtc c                                              21

<210> SEQ ID NO 17
<211> LENGTH: 21
<212> TYPE: DNA
<213> ORGANISM: Artificial sequence
<220> FEATURE:
<223> OTHER INFORMATION: Psmd11 targeting shRNA anti-sense strand
      sequence

<400> SEQUENCE: 17
ataatttcct ttccacgtcg g                                              21

<210> SEQ ID NO 18
<211> LENGTH: 59
<212> TYPE: DNA
<213> ORGANISM: Artificial sequence
<220> FEATURE:
<223> OTHER INFORMATION: PSMD6 targeting shRNA sequence

<400> SEQUENCE: 18
ccggcaggaa ctgtccaggt ttattctcga gaataaacct ggacagttcc tgttttttg     59

<210> SEQ ID NO 19
<211> LENGTH: 59
<212> TYPE: DNA
<213> ORGANISM: Artificial sequence
<220> FEATURE:
<223> OTHER INFORMATION: PSMD6 targeting shRNA sequence

<400> SEQUENCE: 19
ccgggctgga atcatatagg tcattctcga gaatgaccta tatgattcca gcttttttg     59

<210> SEQ ID NO 20
<211> LENGTH: 58
<212> TYPE: DNA
<213> ORGANISM: Artificial sequence
<220> FEATURE:
<223> OTHER INFORMATION: PSMD11 targeting shRNA sequence

<400> SEQUENCE: 20
ccggggacat gcagtcgggt attatctcga gataatacccc gactgcatgt ccttttttg    58

<210> SEQ ID NO 21
<211> LENGTH: 57
<212> TYPE: DNA
<213> ORGANISM: Artificial sequence
<220> FEATURE:
<223> OTHER INFORMATION: PSMD11 targeting shRNA sequence

<400> SEQUENCE: 21
ccggccgacg tggaaaggaa attatctcga gataatttcc tttccacgtc ggttttt       57